United States Patent [19]

Hirai et al.

[11] Patent Number: 5,464,811
[45] Date of Patent: Nov. 7, 1995

[54] BENZENE DERIVATIVES SUBSTITUTED WITH HETEROCYCLIC RING AND HERBICIDES CONTAINING SAME AS ACTIVE INGREDIENTS

[75] Inventors: Kenji Hirai; Mitsuo Yamashita; Tomoko Tateno; Emiko Ejiri; Kikuko Harasawa, all of Kanagawa; Yuichi Onji, Chiba; Sadayuki Ugai, Shizuoka; Shoin Nagato, Saitama, all of Japan

[73] Assignees: Sagami Chemical Research Center, Tokyo; Chisso Corporation, Osaka; Kaken Pharmaceutical Co., Ltd., Tokyo, all of Japan; a part interest

[21] Appl. No.: 409,453

[22] Filed: Mar. 24, 1995

Related U.S. Application Data

[62] Division of Ser. No. 855,694, filed as PCT/JP91/00950, July 16, 1991, Pat. No. 5,424,277.

[30] Foreign Application Priority Data

Jul. 17, 1990 [JP] Japan ................................. 2-187163
Jul. 17, 1990 [JP] Japan ................................. 2-187164

[51] Int. Cl.$^6$ .......................... A01N 43/56; C07D 231/56
[52] U.S. Cl. ........................................ 504/281; 548/360.1
[58] Field of Search ........................ 548/360.1; 504/281

[56] References Cited

U.S. PATENT DOCUMENTS 3,878,224  4/1975  Matsui et al. .

FOREIGN PATENT DOCUMENTS 0049511  10/1981  European Pat. Off. .
0061741  10/1982  European Pat. Off. .
0105721  4/1984  European Pat. Off. .
0308702  3/1989  European Pat. Off. .
2046754  11/1980  United Kingdom .

Primary Examiner—Robert W. Ramsuer
Attorney, Agent, or Firm—Nixon & Vanderhye

[57] ABSTRACT

A benzene derivative substituted with a heterocyclic ring represented by the general formula:

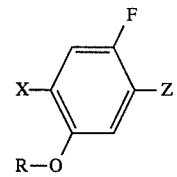

wherein R represents a cycloalkyl group having 3 to 8 carbon atoms, X represents a halogen atom, and Z represents

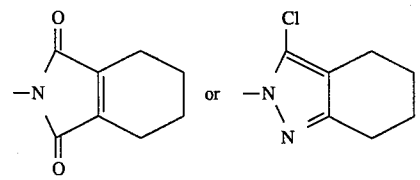

in which said cycloalkyl group may be substituted with an alkyl group having 1 to 6 carbon atoms, a process for preparing the same, and a herbicidal agent comprising the above compound as an active ingredient are disclosed. The compound has an excellent effect in that the compound exhibits a markedly high herbicidal effect on weeds in the field and the paddy field at a low dose and yet exhibits markedly low noxious effects on main crops.

4 Claims, No Drawings

BENZENE DERIVATIVES SUBSTITUTED WITH HETEROCYCLIC RING AND HERBICIDES CONTAINING SAME AS ACTIVE INGREDIENTS

This is a divisional of application Ser. No. 07/855,694, filed as PCT/JP91/00950, July 16, 1991 now U.S. Pat. No. 5,424,277.

FIELD OF UTILITY IN INDUSTRY

The present invention relates to a benzene derivative substituted with a heterocyclic ring represented by the general formula:

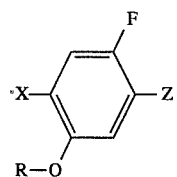

[I]

wherein R represents a cycloalkyl group having 3 to 8 carbon atoms, X represents a halogen atom, and Z represents

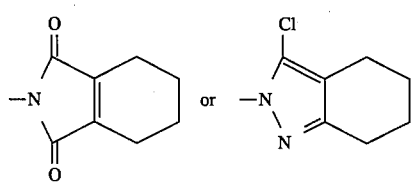

in which the above-described cycloalkyl group may be substituted with an alkyl group having 1 to 6 carbon atoms; a process for preparing the same; and a herbicide containing the same as an active ingredient. More specifically, the present invention relates to an N-substituted-3,4,5,6-tetrahydrophthalimide derivative and an N-substituted phenyl-4,5,6,7-tetrahydro-2H-indazole derivative characterized by having a cycloalkyloxy group at the 5-position of the phenyl ring on the nitrogen atom.

PRIOR ART

Hitherto, as N-substituted phenyl-3,4,5,6-tetrahydrophthalimide derivatives having a herbicidal activity, for example, N-(2-fluoro-4-chloro-5-isopropoxyphenyl)-3,4,5,6-tetrahydrophthalimide (Japanese Patent Publication No. 63-20428) or N-(2-fluoro-4-chloro-5-alkyloxyphenyl)-3,4,5,6-tetrahydrophthalimide (Japanese Patent Application (Kokai) No. 58-72563) have been known, but compounds having cycloalkyloxy group at the 5-position of the phenyl ring on the nitrogen atom have not been known. Also, Japanese Patent Application (Kokai) Nos. 63-68562, 63-68563 and 63-280060 disclose, as examples, the compounds which are different from the compounds of the present invention in the point of having a methyl group in the tetrahydrophthalimide moiety and in which the phenyl ring on the nitrogen atom is substituted with a 2,4-dihalo-5-cycloalkyloxy group, but do not disclose detailed preparation examples and test examples of the activity thereof. Further, Japanese Patent Application (Kokai) No. 55-139359 discloses the compounds which are different from the compounds of the present invention in that the substituent on the 2-position of the phenyl ring is a chlorine atom, but it does not disclose test examples of the activity to be compared.

Tetrahydrophthalimide derivatives known in the prior art exhibit per sea herbicidal activity, but these compounds are not said to be sufficient for use as an active ingredient of a practical herbicidal agents.

On the other hand, with respect to the 2N-substituted phenyl-4,5,6,7-tetrahydro-2H-indazole derivatives, for example, 2N-(2-fluoro-4-chloro-5-isopropoxyphenyl)-4,5,6,7-tetrahydro-2H-indazole (Japanese Patent Application (Kokai) No. 59-59666) or 2N-(2,4-dichloro-5-methoxyphenyl)-4,5,6,7-tetrahydro-2H-indazole (Japanese Patent Application (Kokai) No. 52-51365) is known to have a herbicidal activity. However, these compounds are not said to be sufficient for use as an active ingredient of a practical herbicidal agent.

In recent developments and studies of new agricultural agents, it has been strongly desired to develop novel type agricultural agents which can be replaced for the conventional agricultural agents requiring the treatment at a high dose, in order to avoid environmental contamination and environmental destroy. For this purpose, it is essential to research and study novel compounds which exhibit excellent effects in the treatment at a low dose. Further, it is an important problem to research novel compounds which exhibit a selective herbicidal activity against only weeds and exhibit an excellent performance with markedly reduced noxious effect to the important crops.

DISCLOSURE OF THE INVENTION

As a result of extensive studies by the present inventors to solve the above problems, the present inventors found that the benzene derivatives substituted with a heterocyclic ring represented by the general formula:

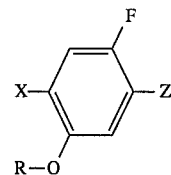

[I]

wherein R represents a cycloalkyl group having 3 to 8 carbon atoms, X represents a halogen atom, and Z represents

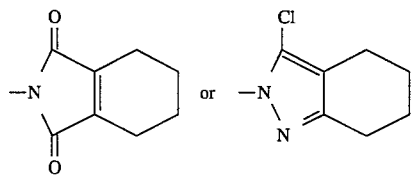

in which the cycloalkyl group may be substituted with an alkyl group having 1 to 6 carbon atoms; possess a high herbicidal effect against weeds in the treatment at a low dose and have markedly reduced noxious effects against the main crops, and completed the present invention.

The compounds of the present invention possess a significantly excellent herbicidal activity in a low dose treatment against various noxious weeds, for example, broadleaved weeds such as common lambsquarters, slender amaranth, velvetleaf and common chickweed, etc. and grass weeds such as barnyardgrass and green foxtail, etc. by foliar application and the soil application in the field, and do not show any herbicide injury which cause problems against main crops, for example, broad-leaf crops such as soybean, cotton, etc. and grass crops such as corn, etc.

Also, the compounds of the present invention exhibit an excellent effect against various noxious weeds in the paddy field, for example, grasses such as early watergrass, etc., broadleaved weeds such as common falsepimpernel, Indian toothcup, waterwort, etc., sedge weeds such as Japanese bulrush, needle spikerush, etc. and Sagitarriapygmaea Miq. etc. in a low dose application, and yet herbicide injury on transplanted rice is very slight. The high selectivity of the compounds of the present invention to the rice plant is not completely unpredictable from the conventional tetrahydrophthalimide derivatives and tetrahydroindazole derivatives, and the characteristic feature thereof is apparently caused by the cycloalkyloxy group introduced into the 5-position of the phenyl ring.

Then, the processes for preparing the compounds of the present invention and the intermediates therefor are described below.

The N-substituted phenyl-8,4,5,6-tetrahydrophthalimide derivative of the present invention can be easily prepared by reacting an aniline derivative represented by the general formula:

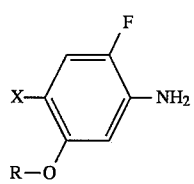

wherein R represents a cycloalkyl group having 3 to 8 carbon atoms, and X represents a halogen atom, in which the cycloalkyl group may be substituted with an alkyl group having 1 to 6 carbon atoms, with 3,4,5,6-tetrahydrophthalic anhydride in an Inert solvent. As the inert solvent, a solvent such as benzene, toluene, xylene, chlorobenzene, acetic acid, etc. or a mixed solvent thereof can be used. The reaction temperature is selected between room temperature and 150° C., and the reaction is preferably carried out at 50 to 120° C. in view of good yields. After the reaction, the desired compound can be easily isolated by routine treatments, and further can be separated in a pure form by recrystallization from an alcohol type solvent such as methanol, etc.

The aniline derivative represented by the general formula (II) as an intermediate can be prepared, for example, by the following two alternative synthetic routes.

Synthetic Route 1

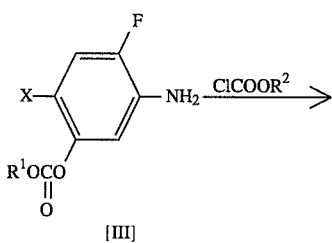

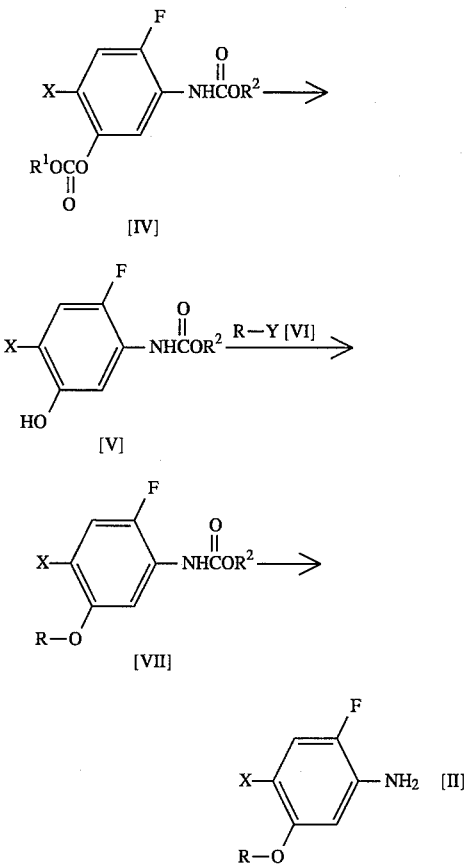

wherein R and X have the same meanings as above, $R^1$ represents an alkyl group having 1 to 6 carbon atoms, $R^2$ represents an alkyl group having 1 to 6 carbon atoms, an allyl group having 3 to 4 carbon atoms or an aralkyl group having 7 to 8 carbon atoms, and Y represents a chlorine atom, a bromine atom, an iodine atom, a methylsulfonyloxy group or a p-tolylsulfonyloxy group.

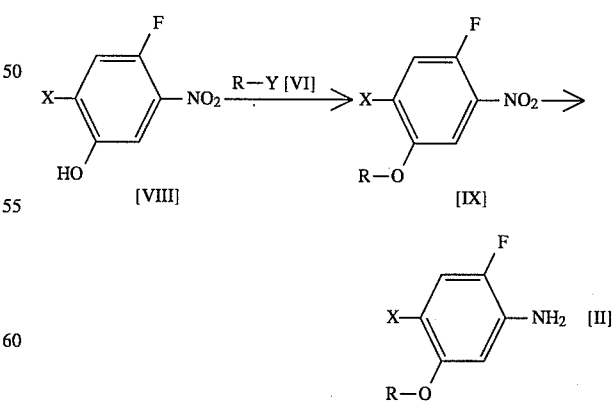

wherein R, X and Y have the same meanings as above.

More specifically, in Synthetic Route 1, an aniline derivative (III) is reacted with a chloroformate ester in the presence of a base such as potassium carbonate, sodium carbonate, magnesium oxide, etc. in a solvent such as acetonitrile, acetone, N,N-dimethylformamide, etc. to convert it into a carbamate derivative (IV). Then, the carbamate derivative (IV) is converted into the phenol derivative (V) by selectively hydrolyzing the carbonate group by the treatment in a protonic solvent in the presence of a base such as sodium hydroxide or potassium carbonate. The resulting phenol derivative (V) is reacted with the compound represented by the general formula R–Y (VI) in the presence of a base such as potassium carbonate, sodium carbonate, magnesium oxide, etc., whereby a cycloalkyloxy group can be introduced at the 5-position of The phenyl ring. The reaction is preferably conducted in an appropriate solvent, and a solvent such as acetonitrile, acetone, methanol, ethanol, N,N-dimethylformamide, etc. can be used. The thus-obtained carbamate derivative (VII) can be converted into the aniline derivative represented by the general formula (II) by the reaction in an aqueous solution of sodium hydroxide thereby hydrolyzing the carbamate ester or, in the case where $R^2$ in the general formula (VII) is, for example, a benzyl group, by the hydrogenolysis using a catalytic reaction with palladium-carbon.

The aniline derivatives represented by the general formula (III) as starting materials are disclosed in Japanese Patent Application (Kokai) No. 62-174065 and can be prepared by the process shown in Reference Examples described hereinafter. The compounds represented by the general formula (VI) are commercially available or can be easily prepared from commercially available compounds.

In Synthetic Route 2, the nitrophenol derivative (VIII) disclosed in Japanese Patent Publication No. 1-61099 is converted into the nitrobenzene derivative represented by the general formula (IX) by reacting it with a compound represented by the general formula R–Y (VI) in the presence of a base such as potassium carbonate, sodium carbonate, magnesium oxide, sodium hydroxide, potassium hydroxide, sodium hydride, sodium methoxide, etc., and then the resulting nitrobenzene derivative can be converted into the aniline derivative (II) by the procedure generally used for reducing an aromatic nitro compound to an amino group, for example, a process using sodium sulfite, a reducing iron, a zinc powder, or a catalytic reduction process using platinum oxide or palladium-carbon.

The N-substituted phenyl-3,4,5,6-tetrahydrophthalimide derivative of the present invention can be prepared by reacting a phenol derivative (X) represented by the general formula:

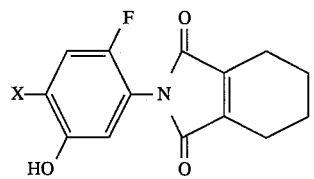

[X]

wherein X has the same meaning as defined above, with a compound represented by the general formula (VI). The reaction is preferably conducted in a solvent such as acetonitrile, N,N-dimethylformamide, acetone, methanol, etc. in the presence of a base such as potassium carbonate, sodium carbonate, magnesium oxide, sodium methoxide, etc.

The phenol derivatives of the general formula (X) as starting materials for the above reaction are disclosed in Japanese Patent Application (Kokai) No. 58-83672, and can be prepared through Synthetic Route 3 hereinafter described.

Synthetic Route 3

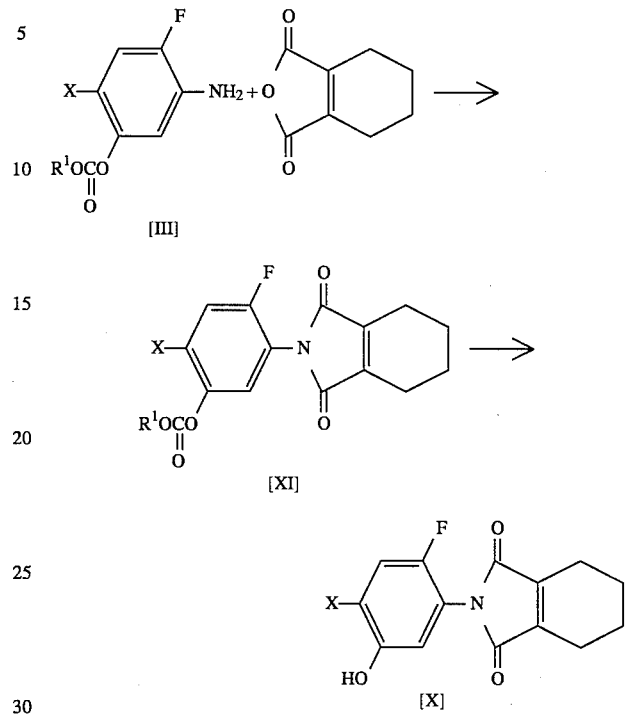

where X and $R^1$ have the same meanings as defined above.

More specifically, the aniline derivative represented by the above formula (III) is reacted with 3,4,5,6-tetrahydrophthalic anhydride in an inert solvent such as benzene, toluene, acetic acid, etc. to convert it into a tetrahydrophthalimide derivative (XI), and then the carbonate group at the 5-position of the phenyl ring thereof is selectively hydrolyzed in the presence of a base whereby a phenol derivative represented by the general formula (X) can be obtained. Examples of the base which can be used include potassium carbonate, potassium hydroxide, sodium hydroxide, etc., and the reaction is preferably conducted in a protonic solvent such as methanol, ethanol, water, etc. at room temperature to about 100° C. from the standpoint of good yields.

The 2N-substituted phenyl-4,5,6,7-tetrahydro-2H-indazole derivatives of the present invention can be prepared, for example, according to the following synthetic route.

Synthetic Route 4

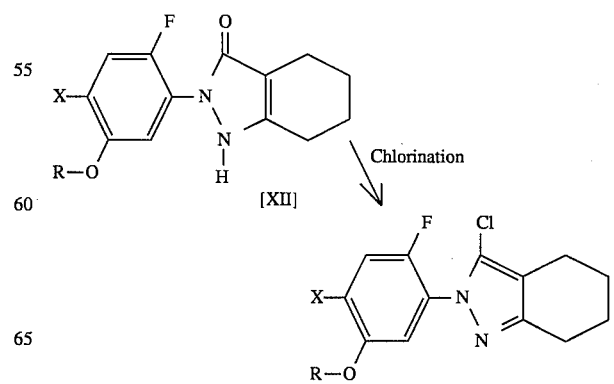

-continued
Synthetic Route 4

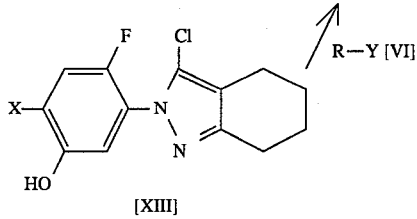
[XIII]

wherein R and X have the same meanings as defined above, and Y represents a chlorine atom, a bromine atom, an iodine atom, a methylsulfonyloxy group or a p-toluenesulfonyloxy group.

More specifically, the indazole derivative of the present invention can be obtained by chlorinating an indazolinone derivative represented by the general formula (XII) using a chlorinating agent such as phosphorus oxy-chloride, phosphorus pentachloride, etc. The reaction may be carried out in an organic solvent, but it is preferably conducted in the absence of the solvent from the standpoint of good yields. The reaction temperature is selected between 100 and 200° C.

Further, the indazole derivative of the present invention can be obtained by reacting a 8-chloro-2N-(2-fluoro-4-halo-5-hydroxyphenyl) 4,5,6,7-tetrahydro-2H-indazole represented by the general formula (XIII) with a compound represented by the general formula (VI) in an appropriate solvent in the presence of a base at a temperature of from room temperature to a heating temperature, preferably at 30 to 100° C. The solvent which can be used includes a solvent such as acetonitrile, acetone, tetrahydrofuran, dioxane, dimethylsulfoxide, N,N-dimethylformamide, methanol, etc. and a mixed solvent thereof. As a base, potassium carbonate, sodium carbonate, magnesium oxide, sodium methoxide, sodium ethoxide, sodium hydride, etc. can be used.

The indazole derivative represented by the general formula (XIII) as a starting material for the preparation is disclosed, for example, in Japanese Patent Application (Kokai) No. 59-170071 and Japanese Patent Application (Kokai) No. 62-80761.

Further, the indazolone derivative represented by the general formula (XII) can be prepared according to the synthetic route shown hereinafter.

Synthetic Route 5

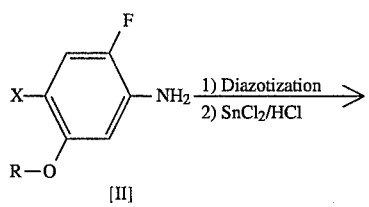
[II]

-continued
Synthetic Route 5

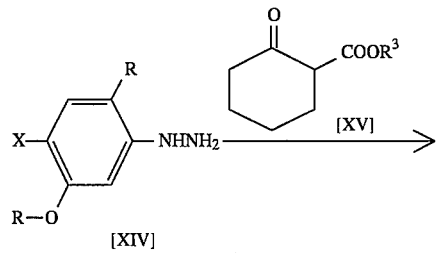
[XIV]

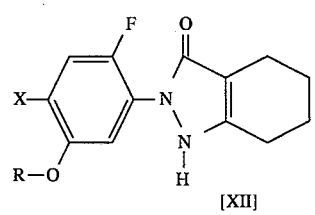
[XII]

wherein R, X and Y have the same meanings as defined above, and $R^3$ represents an alkyl group having 1 to 6 carbon atoms.

More specifically, the aniline derivative (II) which can be prepared by the process shown in Synthetic Route 1 or 2 described above is reacted with sodium nitrite under an acidic condition of hydrochloric acid, sulfuric acid or borofluoric acid to produce a diazonium salt, then reducing the diazonium salt with a reducing agent such as stannous chloride to convert it into a hydrazine derivative (XIV). In the above-described reaction, acetone, acetonitrile, etc. which are used in the preparation of diazonium salts can be used without any problems.

The resulting hydrazine derivative (XIV) can be converted into a 2N-substituted phenyl-1,2,4,5,6,7-hexahydro-3H-indazol-3-one (XII) by subjecting it to a cyclization-condensation reaction with a 2-alkoxycarbonylcyclohexanone represented by the general formula (XV). The reaction is preferably conducted in an organic solvent, such as benzene, toluene, xylene, chlorobenzene, acetic acid, etc. The reaction temperature is preferably higher than the azeotropic temperature of the solvent used and water in view of good reaction efficiency, and the reaction is preferably conducted using an apparatus for removing water such as Dean-Stark apparatus. The reaction proceeds sufficiently without using a catalyst, but is preferably conducted in the presence of a basic compound such as triethylamine, pyridine, etc. since the reaction can be effectively promoted.

Examples of the compounds (I) of the present invention include the compounds shown in Table below.

[Structure I]

X—[benzene ring with F on top, Z on right]—Z
R—O (on bottom)

| Compound No. | X | R |
|---|---|---|

Compounds wherein Z = —N(C=O)(CH2)4(C=O)— (cyclohexene-1,2-dicarboximide)

| Compound No. | X | R |
|---|---|---|
| 1 | F | cyclopropyl group |
| 2 | F | cyclopentyl group |
| 3 | F | 2-methylcyclopentyl group |
| 4 | F | 3-methylcyclopentyl group |
| 5 | F | cyclohexyl group |
| 6 | F | 2-methylcyclohexyl group |
| 7 | F | cycloheptyl group |
| 8 | F | cyclooctyl group |
| 9 | Cl | cyclopropyl group |
| 10 | Cl | cyclopentyl group |
| 11 | Cl | 2-methylcyclopentyl group |
| 12 | Cl | 3-methylcyclopentyl group |
| 13 | Cl | cyclohexyl group |
| 14 | Cl | 2-methylcyclohexyl group |
| 15 | Cl | cycloheptyl group |
| 16 | Cl | cyclooctyl group |
| 17 | Br | cyclopropyl group |
| 18 | Br | cyclopentyl group |
| 19 | Br | 2-methylcyclopentyl group |
| 20 | Br | 3-methylcyclopentyl group |
| 21 | Br | cyclohexyl group |
| 22 | Br | 2-methylcyclohexyl group |
| 23 | Br | cycloheptyl group |
| 24 | Br | cyclooctyl group |

Compounds wherein Z = —N=C(Cl)—N= (fused with cyclohexane ring)

| Compound No. | X | R |
|---|---|---|
| 25 | Cl | cyclopropyl group |
| 26 | Cl | cyclopentyl group |
| 27 | Cl | 2-methylcyclopentyl group |
| 28 | Cl | 3-methylcyclopentyl group |
| 29 | Cl | cyclohexyl group |
| 30 | Cl | 2-methylcyclohexyl group |
| 31 | Cl | cycloheptyl group |
| 32 | Cl | cyclooctyl group |
| 33 | Cl | 2-methylcyclooctyl group |
| 34 | F | cyclopropyl group |
| 35 | F | cyclopentyl group |
| 36 | F | 2-methylcyclopentyl group |
| 37 | F | 3-methylcyclopentyl group |
| 38 | F | cyclohexyl group |
| 39 | F | 2-methylcyclohexyl group |
| 40 | F | cycloheptyl group |
| 41 | F | cyclooctyl group |
| 42 | F | 2-methylcyclooctyl group |
| 43 | Br | cyclopropyl group |
| 44 | Br | cyclopentyl group |
| 45 | Br | 2-methylcyclopentyl group |
| 46 | Br | 3-methylcyclopentyl group |
| 47 | Br | cyclohexyl group |
| 48 | Br | 2-methylcyclohexyl group |
| 49 | Br | cycloheptyl group |
| 50 | Br | cyclooctyl group |

-continued

| Compound No. | X | R |
|---|---|---|
| 51 | Br | 2-methylcyclooctyl group |

The compounds of the present invention possess excellent performance as a herbicidal agent as described above.

In using the compounds of the present invention, as a herbicidal agent, the compounds per se can be used, but, generally they can be used as a herbicidal agent in an admixture with one or more auxiliary agents. Generally, the compounds can be preferably used in the form of preparations, for example, a wettable powder, an emulslfiable agent, a powder, a granule, a flowable agent, etc. in a conventional manner by formulating the compounds with various carriers, diluents, solvents, surface active agents, stabilizers, etc. as auxiliary agents.

The solvent as one of the auxiliary agents in the herbicidal agent comprising the compound of the present invention as an active ingredient suitably include, for example, water, alcohols, ketones, ethers, aliphatic and aromatic hydrocarbons, halogenated hydrocarbons, acid amides, esters, nitriles. The solvent can be used alone or as a mixture of two or more solvents.

The diluents which can be used include mineral powders, e.g., clays such as kaolin and bentonite, talcs such as talc and pyrophyllite, oxides such as diatomaceous earth and white carbon, and vegetable powders such as soybean meal and CMC. Further, surface active agent can be used as a spreading agent, a dispersant, an emulsifying agent and a penetrating agent. The surface active agents include, for example, nonionic surface active agents, cationic surface active agents, and amphoteric surface active agent. These surface active agents can be used alone or as a mixture of two more of the agents according to the utility.

A preferred method for applying the herbicidal agent comprising the compound of the present invention as an active ingredient includes soil treatment, water-surface treatment and Foliar Application. etc. A particularly excellent effect can be obtained by the application before germination or at the germ stage of the weeds to be eliminated.

Also, the herbicidal agent comprising the compound of the present invention as an active ingredient can be used in admixture or in combination with other active ingredients which do not adversely affect the herbicidal activity of the ingredients of the present invention, for example, other herbicidal agents, insecticides, anti-microbial agents, plant growth controlling agents, etc.

The present invention is further illustrated in greater detail by the following Examples, Reference Examples, Preparation Examples and Test Examples, but these examples are not construed as limiting the present invention.

EXAMPLE 1

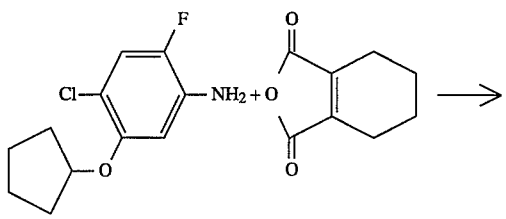

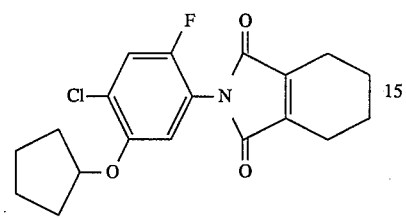

A solution of 2-fluoro-4-chloro-5-cyclopentyloxyaniline (0.50 g, 2.18 mmol) and 3,4,5,6-tetrahydrophthalic anhydride (0.398 g, 2.61 mmol) in acetic acid (3.0 ml) was stirred for 3 hours under refluxing. Water (20 ml) was added to the resulting reaction mixture, and the mixture was extracted with ethyl acetate (20 ml×3 times). The organic layer was dried, and the solvent was distilled off under reduced pressure. The resulting pale yellow oily substance was purified by silica gel column chromatography (development solvent: hexane/ethyl acetate=8/1) to obtain N-(2-fluoro-4-chloro-5-cyclopentyloxyphenyl) 3,4,5,6-tetrahydrophalimide as a colorless transparent oily substance (0.513 g, 1.41 mmol, 65% yield). Ethanol (1.0 ml) was added thereto for recrystallization to obtain the product as a white solid.

Melting point: 69.0°–75.2° C.

$^1$H-NMR Spectrum (CDCl$_3$, TMS, ppm):

δ 1.30–2.10 (12H, m), 2.40 (4H, m), 4.68 (1H, m), 6.75 (1H, d, J$_{HF}$=7.0 Hz), 7.20 (1H, d, J$_{HF}$=9.0Hz)

IR Spectrum (KBr disk, cm$^{-1}$): 1725, 1505, 1430, 1385, 1200.

EXAMPLE 2

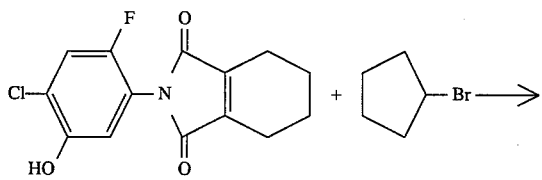

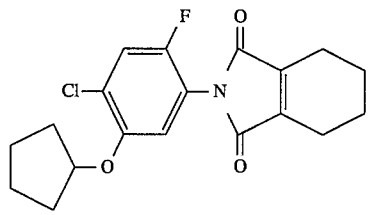

Cyclopentyl bromide (1.2 g, 8.1 mmol) was added to a solution of N-(2-fluoro-4-chloro-5-hydroxyphenyl)-3,4,5,6-tetrahydrophthalimide (2.0 g, 6.76 mmol) and potassium carbonate (0.60 g, 4.34 mmol) in acetonitrile (50 ml), followed by stirring for 2 hours under refluxing. After completion of the reaction, 1N hydrochloric acid (20 ml) was added to the resulting reaction mixture, and the mixture was extracted with ethyl acetate (20 ml×3 times). The organic layer was washed with water, dried over anhydrous magnesium sulfate, and the solvent was distilled off under reduced pressure. Ethanol (5 ml) was added to the resulting pale yellow oily substance, and the precipitated N-(2-fluoro-4-chloro-5-cyclopentyloxyphenyl)-3,4,5,6-tetrahydrophthalimide as a white solid (0.75 g, 2.06 mmol, 30.5% yield) was isolated by filtration. Spectral data and the like are as shown in Example 1.

EXAMPLE 3

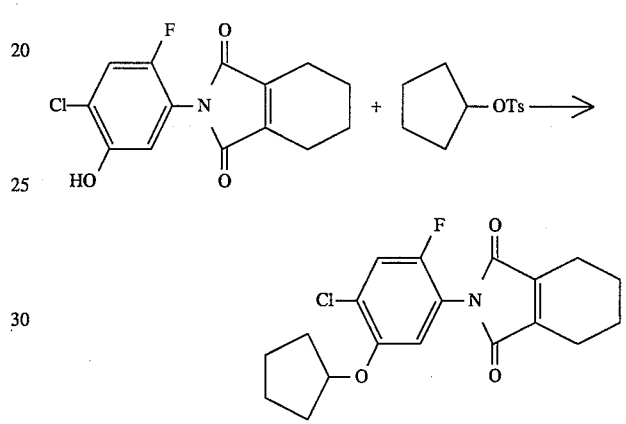

Cyclopentyl p-toluenesulfonate (1.90 g, 8.11 mmol) was added to a solution of N-(2-fluoro-4-chloro-5-hydroxyphenyl)-3,4,5,6-tetrahydrophthalimide (2.0 g, 6.76 mmol) and potassium carbonate (0.60 g, 4.34 mmol) in acetonitrile (50 ml), followed by stirring for 2 hours at 80° C. After completion of the reaction, 1N hydrochloric acid (20 ml) was added to the resulting reaction mixture, and the mixture was extracted with ethyl acetate (20 ml×3 times). The organic layer was washed with water, dried over anhydrous magnesium sulfate, and the solvent was distilled off under reduced pressure. Ethanol (5 ml) was added to the resulting pale yellow oily substance, and the precipitated N-(2-fluoro-4-chloro-5-cyclopentyloxyphenyl)-3,4,5,6-tetrahydrophthalimide as a white solid (0.77 g 2.12 mmol, 31.4% yield) was isolated by filtration. The spectral data and the like are as described in Example 1.

EXAMPLE 4

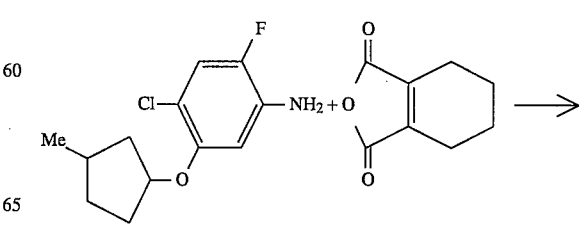

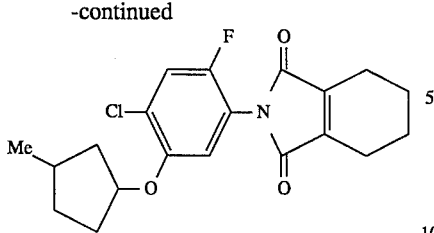

A solution of 2-fluoro-4-chloro-5-(3-methylcyclopentyl)oxyanilline (1.76 g, 7.22 mmol) and 3,4,5,6-tetrahydrophthalic anhydride (1.32 g 8.68 mmol) in acetic acid (15 ml) was stirred for 4 hours under refluxing. The resulting reaction mixture was added to 1N hydrochloric acid (50 ml), and extracted with ether (50 ml×3 times). The organic layer was dried, the solvent was distilled off, and the resulting red brown oily substance was purified by silica gel column chromatography (development solvent: hexane/ethyl acetate=8/1). The resulting N-{2-fluoro-4-chloro-5-(3-methylcyelopentyl)oxyphenyl }-3,4,5,6-tetrahydrophthalimide as a colorless transparent oily substance was recrystallized from methanol to obtain a white solid (0.93 g, 2.38 mmol, 33.0% yield).

Melting point: 68.0°–70.0° C.

$^1$H-NMR Spectrum (CDCl$_3$, TMS, ppm):

δ 1.01 and 1.08 (total 3H, each d, J=6.0 Hz), 1.25–2.20 (11H, m), 2.49 (4H, m), 4.70 (1H, m), 6.72 (1H, d, J$_{HF}$=6.0 Hz), 7.20 (1H, d, J$_{HF}$=9.0Hz).

IR Spectrum (KBr disk, cm$^{-1}$): 1720, 1500, 1430, 1375, 1195.

EXAMPLE 5

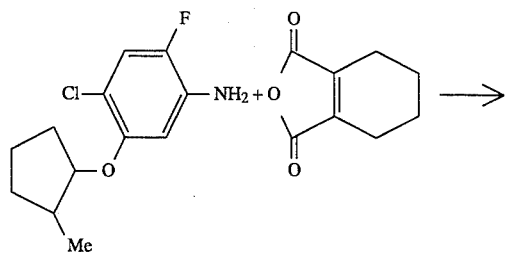

2-Fluoro-4-chloro-5-( 2-methylcyclopentyl) oxyaniline (660 mg, 2.71 mmol), 3,4,5,6-tetrahydrophthalic anhydride (503 mg, 3.31 mmol) and acetic acid (10 ml) were charged into a 50 cc round-bottom flask, and heated for 5 hours while refluxing. After completion of the reaction, the reaction solution was cooled to room temperature, and poured into ice-water (100 ml). The mixture was extracted with ethyl acetate (30 ml×3), and the organic layers were combined, washed with water and a saturated aqueous solution of sodium chloride, and dried over anhydrous magnesium sulfate. The drying agent was separated by filtration, the solvent was distilled off under reduced pressure, and the resulting pale brown oily substance was purified by silica gel column chromatography (development solvent: hexane/ethyl acetate=9/1) to obtain N-{2-fluoro-4-chloro-5-(2-methylcyclopentyl)oxyphenyl}-3,4,5,6-tetrahydrophthalimide (1.00 g, 2.65 mmol, 98% yield)

Colorless transparent oily substance $^1$H-NMR Spectrum (CDCl$_3$, TMS, ppm):

δ 1.13 (3H, d, J=7.0 Hz), 1.40–2.15 (10H, m), 2.25–2.50 (4H, m), 4.25 (1H, m), 4.52 (1H, m), 6.72 (1H, d, J$_{HF}$=7.3 Hz), 7.30 (1H, d, J$_{HF}$=10.2 Hz).

IR Spectrum (neat, cm$^{-1}$): 2970, 1725, 1500, 1425, 1375, 1195.

EXAMPLE 6

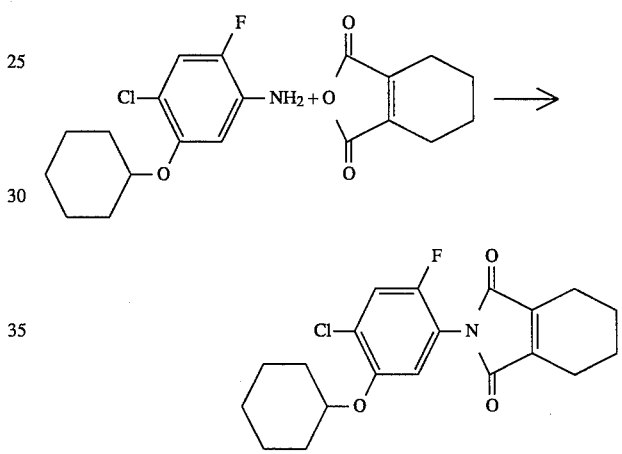

2-Fluoro-4-chloro-5-cyclohexyloxyaniline (213 mg, 0.874 mmol), 3,4,5,6-tetrahydrophthalic anhydride (134 mg, 0.874 mmol) and acetic acid (10 ml) were charged into a 50 cc round-bottom flask, and heated for 15 hours while refluxing. After completion of the reaction, the reaction solution was cooled to room temperature, water (50 ml) was added thereto, and extracted with ethyl acetate (20 ml×3). The organic layers were combined, washed with water and a saturated aqueous solution of sodium chloride, and dried over anhydrous magnesium sulfate. The drying agent was separated by filtration and the solvent was distilled off under reduced pressure to obtain a crude product (332 mg). The product was purified by silica gel column chromatography (development solvent: hexane/ethyl acetate=19/1) to obtain N-(2-fluoro-4-chloro-5-cyclohexyloxyphenyl) 3,4,5,6-tetrahydrophthalimide as a white solid (230 mg, 0.609 mmol, 70% yield). By recrystallization of the product from hexane/chloroform, it was isolated as white needle crystals.

Melting point: 102.0°–103.0° C.

$^1$H-NMR Spectrum (CDCl$_3$, TMS, ppm):

δ 1.20–2.05 (14H, m), 2.25–2.50 (4H, m), 4.18 (1H, m), 6.79 (1H, d, J$_{HF}$×7.3 Hz) 7.23 (1H, d, J$_{HF}$=10.2 Hz).

IR Spectrum (KBr disk, cm$^{-1}$): 2950, 1715, 1495, 1425, 1375, 1190.

EXAMPLE 7

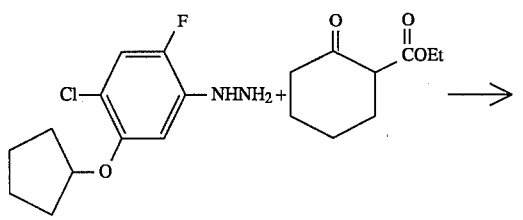

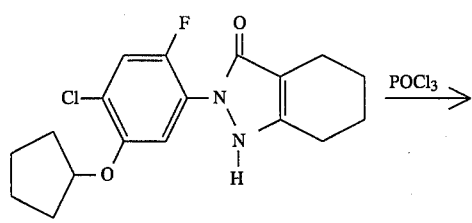

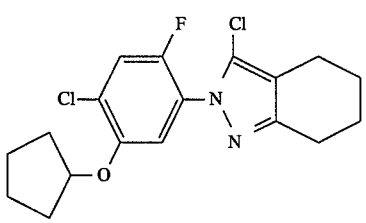

2-Fluoro-4-chloro-5-cyclopentyloxyphenylhydrazine (24.5 g, 0.10 mol), 2-ethoxycarbonylcyclohexanone (17.0 g, 0.10 mol) were dissolved in acetic acid (200 ml), and stirred for 2 hours while heating under refluxing. After completion of the reaction, the solvent was distilled off to obtain a crude product (37 g). The product was washed with a mixed solvent of benzene/hexane to obtain 2N-(2-fluoro-4-chloro-5-cyclopentyloxyphenyl)-1,2,4,5,6,7-hexahydro-3H indazol-3-one as a white solid (25.8 g, 72.3% yield).

Melting point: 151°–152° C.

$^1$H-NMR Spectrum (CDCl$_3$-CF$_3$CO$_2$H, TMS, ppm):

δ 1.40–2.03 (12H, m), 2.37 (2H, m), 2.55 (2H, m), 4.65 (1H, m), 6.97 (1H, d, J$_{HF}$=6.0 Hz), 7.18 (1H, d, J$_{HF}$=9.0 Hz).

IR Spectrum (KBr disk, cm$^{-1}$): 2950, 2400, 1770, 1600, 1505, 880.

MS Spectrum (m/e): 352 (M$^+$, 6%), 350 (M$^+$, 18%), 284 (100%), 81 (38%), 41 (66%).

Phosphorus oxychloride (6.6 g, 43.0 mmol) was added to the resulting 2N-(2-fluoro-4-chloro-5-cyclopentyloxyphenyl)-1,2,4,5,6,7-hexahydro-3H-indazol-3-one (15.0 g, 42.8 mmol), followed by stirring for 30 minutes while heating at 160° C. After cooling the reaction solution, an ice-cooled dilute aqueous solution of sodium hydroxide (50 ml) was added thereto, and the mixture was extracted with methylene chloride (200 ml×4). The extract was washed with a dilute aqueous sodium hydroxide (400 ml) and a saturated aqueous solution of sodium chloride (400 ml), and dried over anhydrous magnesium sulfate. The solvent was distilled off under reduced pressure, and the residue was purified by silica gel column chromatography (development solvent: ethyl acetate/hexane=1/9–1/5) to obtain 3-chloro-2N-(2-fluoro-4-chloro-5-cyclopeneyloxyphenyl) 4,5,6,7-tetrahydro-2H-indazole as a white solid (4.3 g, 26.5% yield).

Melting point: 88°–91° C.

$^1$H-NMR Spectrum (CDCl$_3$, TMS, ppm):

δ 1.05–2.10 (12H, m), 2.30–2.85 (4H, m), 4.73 (1H, m), 6.95 (1H, d, J$_{HF}$=6.0 Hz) 7.23 (1H, d, J$_{HF}$=9.0 Hz).

IR Spectrum (KBr disk, cm$^{-1}$): 2960, 1510, 1195,

MS Spectrum (m/e) 372 (M$^+$, 12.1%), 370 (M$^+$, 11.6%), 368 (M$^+$, 17.0%), 300 (100%), 265 (52.7%), 41 (64%).

Elementary Analysis (Calculated values: C$_{18}$H$_{19}$N$_2$OClF %):

C, 58.39 (58.55);
H, 5.04 (5,19);
N, 7.49 (7.59).

EXAMPLE 8

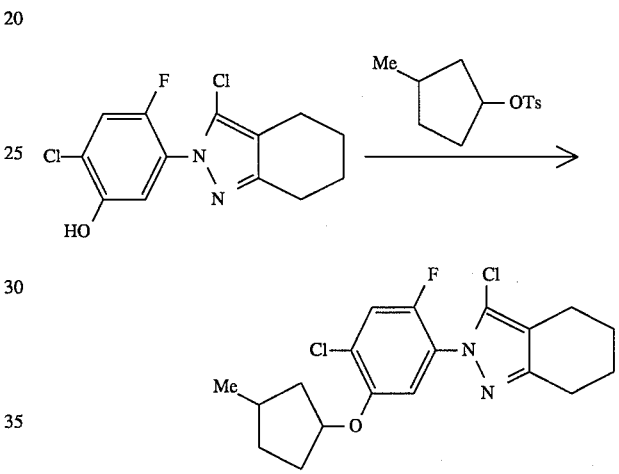

A solution of 3-chloro-2N-(2-fluoro-4-chloro-5-hydroxyphenyl)-4,5,6,7-tetrahydro-2H-indazole (220 mg, 0.731 mmol), 3-methylcyclopentyl p-toluenesulfonate (250 mg, 0.999 mmol) and potassium carbonate (120 mg, 0.870 mmol) in acetonitrile (25 ml) was stirred for 4 hours while heating under refluxing. After completion of the reaction, the reaction solution was poured into 1N hydrochloric acid (50 ml), and extracted with ethyl acetate (50 ml×3). The organic layer was washed with a saturated aqueous solution of sodium chloride (100 ml) and dried over magnesium sulfate. The drying agent was separated by filtration, and the solvent was distilled off from the filtration obtain a crude product (0.29 g). The product was purified by silica gel column chromatography (development solution: ethyl acetate/hexane=1/9) to obtain 3-chloro-2N-{2-Fluoro=4-chloro-5-(3-methylcyclopentyl) oxyphenyl}-4,5,6,7-hexahydro-2H-indazole as a white solid (242 mg, 86.4% yield).

$^1$H-NMR Spectrum (CDCl$_3$, TMS, ppm):

δ 1.03 and 1.08 (total 3H, each d, J=6.0 Hz), 1.17–2.4 (11H, m), 2.4–2.83 (4H, m), 4.80 (1H, m), 6.98 (1H, d, J$_{HF}$=6.0 Hz), 7.38 (1H, d, J$_{HF}$=9.0 Hz).

IR Spectrum (neat, cm$^{-1}$): 2970, 1505, 1200.

REFERENCE EXAMPLE 1

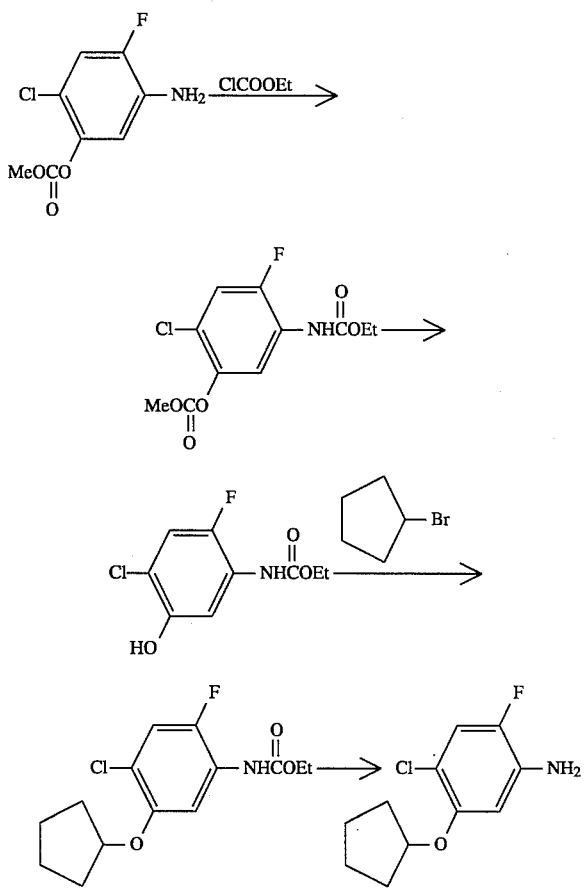

Ethyl chloroformate (16.3 g, 150 mmol) was added to a solution of 2-fluoro-4-chloro-5-methoxycarbonyloxyaniline (22.0 g, 100 mmol) and potassium carbonate (13.8g, 100 mmol) in acetone (300 ml), followed by stirring for 5 hours at 60° C. After completion of the reaction, the solvent was distilled off under reduced pressure, and the residue was made acidic by adding 1N hydrochloric acid (100 ml) and extracted with ethyl acetate (100 ml×3). The organic layer was washed with water, dried, and the solvent was distilled off under reduced pressure. The precipitated solid was isolated by filtration.

The solid was recrystallized from chloroform-hexane to obtain ethyl N-(2-fluoro-4-chloro-5-methoxycarbonyloxyphenyl)carbamate as white crystals (23.3 g, 80.2% yield).

Melting point: 143.8°–147.2° C.

$^1$H-NMR Spectrum (CDCl$_3$, TMS, ppm):

δ 1.13 (3H, t, J=6.5 Hz), 3.92 (3H, s), 4.23 (2H, q, J=6.5 Hz). 6.80 (1H, br s), 7.15 (1H, d, J$_{HF}$=10.5 Hz), 8.12 (1H, d, J$_{HF}$=8.0 Hz).

IR Spectrum (KBr disk, cm$^{-1}$): 1770, 1730, 1545, 1290, 1235, 1215.

The resulting ethyl N-(2-fluoro-4-chloro-5-methoxycarbonyloxyphenyl)carbamate (45.2 g, 155 mmol) was reacted with potassium carbonate (21.4 g, 155 mmol) and water (100 ml) for 2 hours while heating under refluxing. After completion of the reaction, the mixture was cooled to room temperature, the solvent was distilled off under reduced pressure. The residue was made acidic by adding 1N hydrochloric acid (300 ml), and extracted with ethyl acetate (100 ml×3 times). The organic layer was washed with water, dried, the solvent was distilled off under reduced pressure, and the precipitated solid was isolated by filtration. The solid was recrystallized from chloroform-hexane to obtain ethyl N-(2-fluoro-4-chloro-5-hydroxyphenyl)carbamate as white crystals (35.2 g, 97% yield).

Melting point: 151.5°–154.2° C.

$^1$H-NMR Spectrum (CDCl$_3$, TMS, ppm):

δ 1.32 (3H, t, J=7.2 Hz), 4.23 (2H, q, J=7.2 Hz), 5.84 (1H, s) 6.80 (1H, br s), 7.04 (1H, d, J$_{HF}$=10.5 Hz), 7.85 (1H, d, J$_{HF}$=7.5 Hz).

IR Spectrum (KBr, cm$^{-1}$): 3440, 1710, 1560, 1430, 1250.

Then, a solution of the resulting ethyl N-(2-fluoro-4-chloro-5-hydroxyphenyl)carbamate (10.0 g, 42.8 mmol) and potassium carbonate (8.87 g, 64.2 mmol) in acetonitrile (150 ml) was stirred for 1 hour at 80° C. Then, cyclopentyl bromide (9.57 g, 84.2 mmol) was added dropwise thereto, followed by reacting for further 7 hours. After completion of the reaction, the solvent was distilled off under reduced pressure, and the residue was made acidic by adding 1N hydrochloric acid (100 ml) and extracted with ethyl acetate (100 ml×8 times). The organic layer was washed with water, dried, and the solvent was distilled off under reduced pressure to obtain ethyl N-(2-fluoro-4-chloro-5-cyclopentyloxyphenyl)carbamate (12.7 g, 98% yield).

Melting point: 92.8°–97.8° C.

$^1$H-NMR Spectrum (CDCl$_3$, TMS, ppm):

δ 1.33 (3H, t, J=7.0 Hz), 1.40–2.10 (8H, m) 4.32 (2H, q, J=7.0 Hz), 4.88 (1H, m), 6.87 (1H, br s ), 7.15 (1H, d, J$_{HF}$=10.5 Hz ), 7.92 (1H, d, J$_{HF}$=7.0 Hz).

IR Spectrum (KBr, cm$^{-1}$): 1710, 1535, 1495, 1415, 1255.

When cyclopentyl p-tolylsulfonate was used in place of cyclopentyl bromide in the above reaction, the desired ethyl N-(2-fluoro-4-chloro-5-cyclopentyloxyphenyl)carbamate could be obtained in a yield of 95%.

Ethyl alcohol (50 ml) and a 2N aqueous solution of sodium hydroxide (100 ml) were added to the thus-obtained ethyl N-(2-fluoro-4-chloro-S-cyclopentyloxyphenyl)carbamate, followed by stirring for 4 hours while heating in an oil bath at 110° C. After completion of the reaction, the solvent was distilled off, and the residue was extracted with ethyl acetate (100 ml×3 times). The organic layer was washed with a saturated aqueous sodium chloride, dried, and the solvent was distilled off under reduced pressure to obtain 2-fluoro-4-chloro-5-cyclopentyloxyaniline (9.36 g, 40.8 mmol, 97% yield).

$^1$H-NMR Spectrum (CDCl$_3$, TMS, ppm):

δ 1.40–2.07 (8H, m), 3.72 (2H, br s), 4.57 (1H, m), 6.35 (1H, d, J$_{HF}$=8.0 Hz), 6.98 ,(1H, d, J$_{HF}$=10.5 Hz).

IR Spectrum (KBr, disk, cm$^{-1}$): 2980, 1635, 1510, 1423, 1250, 1190.

REFERENCE EXAMPLE 2

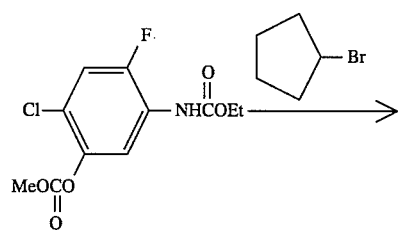

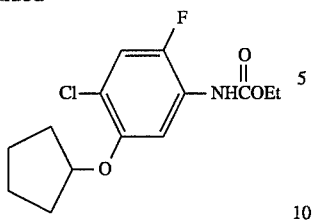

Ethyl N-(2-fluoro-4-chloro-5-methoxycarbonyloxyphenyl)carbamate (1.45 g, 4.97 mmol) prepared by the process described in Reference Example 1 and a solution of potassium carbonate (1.03 g, 7.46 mmol) in ethanol (50 ml) were stirred for 1 hour while refluxing, and then cyclopentyl bromide (1.11 g, 7.46 mmol) was added thereto, followed by further stirring for 2 hours. After completion of the reaction, the mixture was poured into 1N hydrochloric acid (50 ml), and extracted with ethyl acetate (50 ml×3 times). The organic layer was dried, and concentrated under reduced pressure to obtain ethyl N-(2-fluoro-4-chloro-5-cyclopentyloxyphenyl)carbamate as grey white crystals (1.41 g, 4.69 mmol, 94.4% yield). The spectral data and the like are as shown in Reference Example 1.

REFERENCE EXAMPLE 3

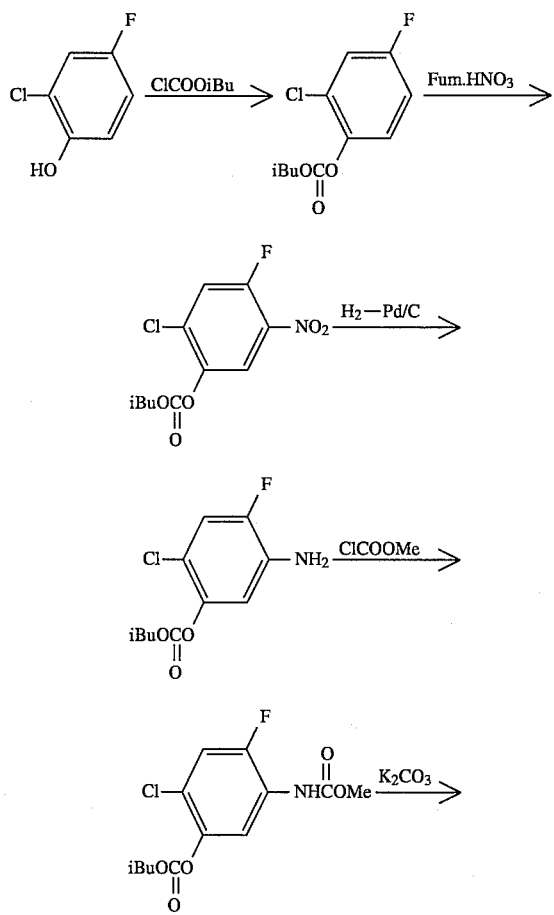

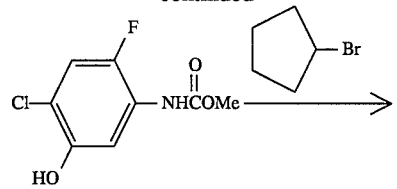

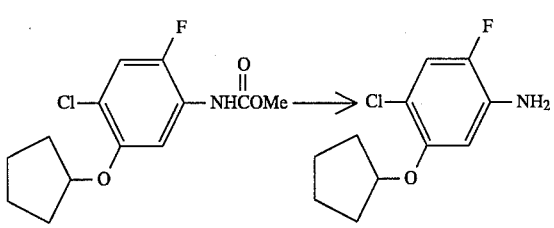

2-Chloro-4-fluorophenol (29.3 g, 0.20 mmol) was charged into a 300 cc round-bottom flask equipped with a dropping funnel, and a 2N-NaOH aqueous solution (100 ml) was added thereto under ice-cooling, followed by stirring for 30 minutes. Then, isobutyl chloroformate (30 ml, d=1.053, 31.6 g, 0.23 mol) was added dropwise thereto, the mixture was stirred for 2 hours while gradually elevating the temperature to room temperature. After completion of the reaction, the mixture was extracted with methylene chloride (100 ml×3 times) and dried over anhydrous magnesium sulfate. After removing the drying agent, the solvent, etc. was distilled off under reduced pressure to obtain 2-chloro-4-fluorophenyl(isobutyl)carbonate as a colorless transparent oil (45.8 g, 0.186 mmol, 93.0% yield).

$^1$H-NMR (CDCl$_3$, TMS, ppm):

δ 1.00 (6H, d, J=6.9 Hz), 2.05 (1H, t & sep, J=6.3 and 6.9 Hz), 4.05 (2H, d, J=6.3 Hz), 6.8–7.3 (3H, m).

Then, fuming nitric acid (100 ml, 98%, d=1.52) was charged into a 200 cc round-bottom flask, and 2-chloro-4-fluorophenyl(isobutyl)carbonate (10 g, 40.5 mmol) was slowly added thereto under ice-cooling. After stirring as it was for 30 minutes, the reaction mixture was poured onto ice. The precipitated 2-fluoro-4-chloro-5-isobutyloxycarbonyloxynitrobenzene as a pale yellow solid was filtered, and washed with water. By thoroughly drying, the desired compound was obtained as white crystals (10.8 g, 36.9 mmol, 91.0% yield).

Melting point: 38.0°–40.0° C.

$^1$H-NMR (CDCl$_3$, TMS, ppm):

δ 1.00 (6H, d, J=6.9 Hz), 2.07 (1H, t & sep, J=6.3 and 6.9 Hz), 4.07 (2H, d, J=6.3 Hz), 7.42 (1H, d, J$_{HF}$=10.2 Hz). 8.02 (1H, d, J$_{HF}$=6.9 Hz).

The thus-obtained 2-Fluoro-4-chloro-5-isobutyloxycarbonyloxynitrobenzene (10 g, 34.3 mmol), toluene (100 ml) as a solvent and 10% Pd/C (1.5 g) were charged into a 300 cc pressure-resistant glass autoclave. After replacing the inside thoroughly with a hydrogen gas, stirring was started under a hydrogen pressure of 4 arms. Heat was generated (up to about 50° C.) as the reaction proceeds, and the stirring was continued as it was. Further, the stirring was continued while occasionally adding hydrogen until the absorption of hydrogen ceased. After completion of the reaction, Pd/C was separated by filtration, and liberated water was removed with a drying agent. The solvent was distilled off under reduced pressure to obtain quantitatively substantially pure 2-chloro-4-fluoro-5-isobutyloxycarbonyloxyaniline (9.42 g) as a yellow oil.

¹H-NMR Spectrum (CDCl₃, TMS, ppm):

δ 1.00(6H, d, J=6.9 Hz), 2.04 (1H, t & sep, J=6.3 and 6.9 Hz), 4.04 (2H, d, J=6.3 Hz), 6.97 (1H, d, $J_{HF}$=6.9 Hz), 7.24 (1H, d, $J_{HF}$=9.0 Hz).

Methyl chloroformate (23.4 g, 0.248 mol) was added to a solution of 2-fluoro-4-chloro-5-isobutyloxycarbonyloxyanlline (65.0 g, 0.248 mol) and potassium carbonate (32 g, 0.232 mmol) in acetone (300 ml), followed by stirring for 5 hours under refluxing. After completion of the reaction, the solvent was distilled off under reduced pressure, 1N hydrochloric acid (300 ml) was added thereto, and the precipitated solid was filtered. The solid was washed thoroughly with water and dried to obtain methyl N-(2-fluoro-4-chloro-5-1sobutyloxycarbonyloxyphenyl)carbamate as white crystals (56.6 g, 71.4% yield).

Melting point: 72.2°14 78.8° C.

¹H-NMR Spectrum (CDCl₃, TMS, ppm):

δ 1.00(6H, d, J=6.5 Hz), 2.05 (1H, t & sep, J=6.5 Hz), 3.78 (3H, s), 4.03 (2H, d, J=6.5 Hz), 6.85 (1H, br, s), 7.08 (1H, d, $J_{HF}$=10.2 Hz), 8.10 (1H, d, $J_{HF}$=7.5 Hz).

IR Spectrum (KBr disk, cm⁻¹): 1773, 1733, 1545, 1285, 1235, 1180.

Methyl N-(2-fluoro-4-chloro-5-isobutyloxycarbonyloxyphenyl)carbamate (14.0 g. 48.8 mmol) obtained as described above was dissolved in methanol (100 ml), and then sodium carbonate (7.26 g, 52.3 mmol) was added thereto, followed by reacting at 50° C. for 3 hours. After completion of the reaction, the solvent was distilled off under reduced, and the resulting solid was dissolved in acetic acid (20 ml). The solution was poured into ice-water, and the precipitated solid was isolated by filtration. The solid was washed thoroughly with water and dried to obtain methyl N-(2-fluoro-4-chloro-5-hydroxyphenyl)carbamate as white crystals (9.60 g, 43.7 mmol, 99.8%).

Melting point: 140.0°–141.0° C.

¹H-NMR Spectrum (CDCl₃, TMS, ppm):

δ 1.57 (3H, s), 3.78 (3H, s), 5.53 (1H, s), 6.75 (1H, br, s), 7.05 (1H, d, $J_{HF}$=10.5 Hz), 7.82 (1H, d, $J_{HF}$=7.5 Hz).

IR Spectrum (KBr disk, cm⁻¹): 3440, 1717, 1560, 1430, 1250.

A solution of methyl N-(2-fluoro-4-chloro-5-hydroxyphenyl)carbamate (5.0 g, 22.8 mmol) obtained as described above and potassium carbonate (3.89 g, 28.1 mmol) in acetonitrile (50 ml) was stirred for 1 hour under refluxing. Then, bromocyclopentane (4.07 g, 27.3 mmol) was added dropwise thereto, and the mixture was further reacted for 3 hours. After completion of the reaction, the solvent was distilled off, the residue was made acidic by adding 1N hydrochloric acid (100 ml), and extracted with ethyl acetate (100 ml×3 times). The organic layer was washed with water, dried, and the solvent was distilled off under reduced pressure to obtain methyl N-(2-fluoro-4-chloro-5-cyclopentyloxyphenyl)carbamate (5.56 g, 19.8 mmol, 84.7% yield).

Melting point: 120.0°–123.0° C.

¹H-NMR Spectrum (CDCl₃, TMS, ppm):

δ 1.40–2.10 (8H, m), 3.77 (3H, s), 4.77 (1H, m), 6.82 (1H, br, s), 7.07 (1H, d, $J_{HF}$=10.5 Hz), 7.83 (1H, d, $J_{HF}$=7.5 Hz).

IR Spectrum (KBr disk, cm⁻¹): 1714, 1535, 1500, 1415, 1255, 1190.

Ethyl alcohol (30 ml) and a 2N aqueous solution of sodium hydroxide (50 ml) were added to methyl N-(2-fluoro-4-chloro-5-cyclopentyloxyphenyl)carbamate obtained above, and the mixture was stirred For 4 hours while heating on an oil bath at 110° C. After completion of the reaction, the solvent was distilled off, and the residue was extracted with ethyl acetate (100 ml×3 times). The organic layer was washed with a saturated aqueous solution of sodium chloride, dried, and the solvent was distilled off under reduced pressure to obtain oily 2-fluoro-4-chloro-5-cyclopentyloxyaniline (4.38 g, 19.0 mmol, 95.0% yield). The spectral data and the like are as shown in Reference Example 1.

REFERENCE EXAMPLE 4

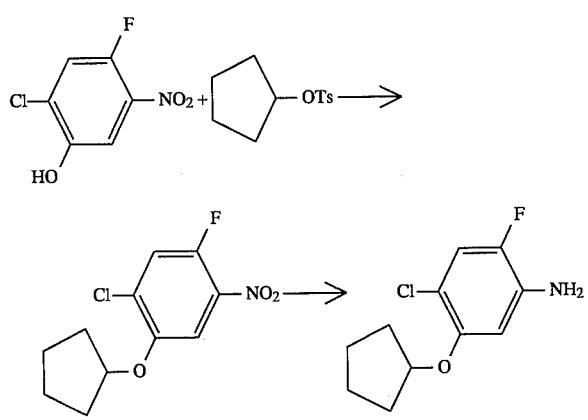

A solution of 2-fluoro-4-chloro-5-hydroxynitrobenzene (7.1 g, 37.1 mmol) and potassium carbonate (5.1 g, 37.1 mmol) in acetonitrile (300 ml) was stirred for 2 hours at a refluxing temperature. Cyclopentyl p-toluenesulfonate (10.3 g, 40.8 mmol) was added thereto, followed by stirring further for 2 hours under refluxing. After completion of the reaction, the solvent was distilled off under reduced pressure from the reaction mixture, 1N hydrochloric acid (800 ml) was added thereto, and the mixture was extracted with ethyl acetate (100 ml×3 times). The organic layer was washed with an aqueous solution of sodium bicarbonate and water, dried, and the solvent was distilled off under reduced pressure to obtain 2-fluoro-4-chloro-5-cyclopentyloxynitrobenzene as a yellow solid (8.93 g, 34.3 mmol, 92.6% yield).

Melting point: 58.0°–62.6° C.

¹H-NMR Spectrum (CDCl₃, TMS, ppm):

δ 1.41–2.26 (8H, m), 4.87 (1H, m), 7.34 (2H, d, $J_{HF}$=10.5 Hz), 7.62 (2H, d, $J_{HF}$=7.5 Hz).

IR Spectrum (KBr disk, cm⁻¹): 1535, 1490, 1350, 1205.

The resulting 2-fluoro-4-chloro-5-cyclopentyloxynitrobenzene (13.0 g, 50.1 mmol) was dissolved in toluene (100 ml), a catalytic amount of 10% palladium-carbon (0.5 g) was added thereto, and the mixture was reacted at room temperature to 70° C. under a hydrogen pressure of 3 to 5 arms. in a glass autoclave. After absorption of hydrogen gas ceased, the catalyst was removed by filtration, and the solvent was distilled off under reduced pressure from the filtrate to obtain substantially quantitatively oily 2-fluoro-4-chloro-5-cyclopentyloxyaniline. The spectral data and the like are as described in Reference Example 1.

REFERENCE EXAMPLE 5

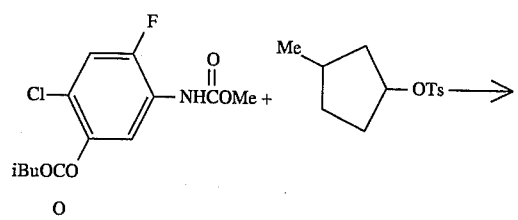

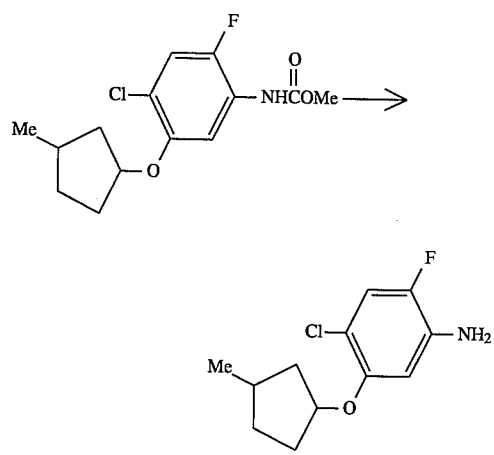

A solution of methyl N-(2-fluoro-4-chloro-5-isobutyloxycarbonyloxyphenyl)carbamate (5.37 g, 16.8 mmol) prepared by the process as shown in Reference Example 3, 3-methylcyclopentyl p-toluenesulfonate (5.0 g, 20.2 mmol) and potassium carbonate (2.32 g, 16.8 mmol) in methanol (50 ml) was stirred for 5 hours under refluxing. After completion of the reaction, the reaction mixture was poured into 1N hydrochloric acid (100 ml), and the mixture was extracted with ethyl acetate (50 ml×3 times). The organic layer was dried, and the solvent was distilled off under reduced pressure to obtain methyl N-{2-fluoro-4-chloro-5-(3-methylcyclopentyl)oxyphenyl} carbamate as grey white crystals (3.81 g, 12.6 mmol, 75.2% yield).

$^1$H-NMR Spectrum (CDCl$_3$, TMS, ppm):

δ 1.02 and 1.08 (total 3H, d, J=6.0 Hz), 1.25–2.40 (7H, m), 3.77 (3H, s), 4.75 (1H, m), 6.68 (1H, br s), 7.05 (1H, d, J$_{HF}$=10.5 Hz), 7.75 (1H, d, J$_{HF}$=7.5 Hz).

Then, ethyl alcohol (20 ml) and a 2N aqueous solution of sodium hydroxide (30 ml) were added to the resulting methyl N-{2-fluoro-4-chloro-S-(3-methylcyclopentyl)oxyphenyl} carbamate (3.45 g, 11.4 mmol), followed by stirring for 3 hours under refluxing. After completion of the reaction, the reaction mixture was extracted with ethyl acetate (50 ml×3 times). The organic layer was washed with a saturated aqueous sodium chloride solution, dried, and the solvent was distilled off under reduced pressure to obtain 2-fluoro-4-chloro-5-(3-methylcyclopentyl)oxyaniline (1.77 g, 7.26 mmol, 63.6% yield).

$^1$H-NMR Spectrum (CDCl$_3$, TMS, ppm):

δ 1.02 and 1.10 (total 3H, d, J=6.0 Hz), 1.22–2.58 (7H, m), 3.75 (2H, br, s), 4.65 (1H, m), 6.33 (1H, d, J$_{HF}$=8.0 Hz), 6.98 (1H, d, J$_{HF}$=10.0 Hz).

REFERENCE EXAMPLE 6

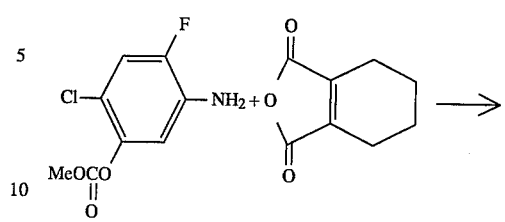

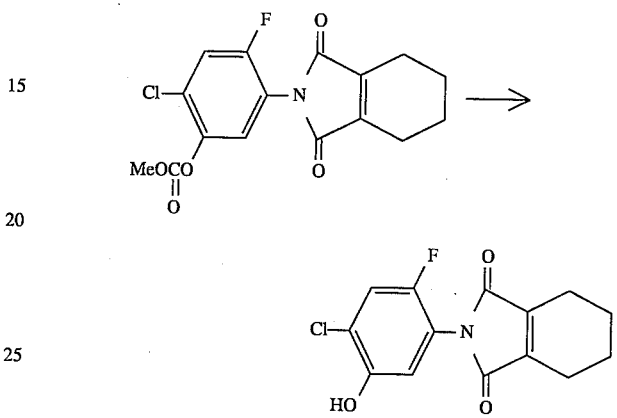

A solution of 2-fluoro-4-chloro-5-methoxycarbonyloxyaniline (20.0 g, 91.1 mmol) and 3,4,5,6-tetrahydrophthalic anhydride (14.0 g, 92.0. mmol) in acetic acid (200 ml) was reacted for 5 hours while heating under refluxing. After completion of the reaction, the mixture was cooled to room temperature, water (200 ml) was added thereto, and extracted with ethyl acetate (100 ml×3 times). The organic layer was washed with an aqueous solution of sodium carbonate and water, dried, and the solvent was distilled off under reduced pressure. The resulting oily substance was purified by silica gel column chromatography (development solvent: ethyl acetate/hexane=1/5) to obtain N-(2-fluoro-4-chloro-5-methoxycarbonyloxyphenyl)-3,4,5,6-tetrahydrophthalimide as a white solid (26.2 g, 72.1 mmol, 79.2% yield).

Melting point: 138.5°–146.2° C.

$^1$H-NMR Spectrum (CDCl$_3$, TMS, ppm):

δ 1.82 (4H, m), 2.42 (4H, m), 3.93 (3H, s), 7.21 (1H, d, J$_{HF}$=6.5 Hz), 7.33 (1H, d, J$_{HF}$=9.0 Hz).

IR Spectrum (KBr disk, cm$^{-1}$): 1765, 1725, 1508, 1500, 1440, 1430, 1260, 1195.

Potassium carbonate (4.6 g, 33.3 mmol) was added to a solution of N-(2-fluoro-4-chloro-5-methoxycarbonyloxyphenyl)-3,4,5,6-tetrahydrophthalimide (11.8 g, 33.4 mmol) obtained as described above in methanol (100 ml), followed by stirring for 5 hours under refluxing. After completion of the reaction, the mixture was poured into 1N hydrochloric acid (200 ml), and the mixture was extracted with ethyl acetate (100 ml×3 times). The organic layer was washed with water, dried, and the solvent was distilled off under reduced pressure to obtain a crude product (9.4 g). The product was recrystallized from ether/hexane to obtain N-(2-fluoro-4-chloro-5-hydroxypheyl) 3,4,5,6-tetrahydrophthalimide as a white solid (6.7 g 22.7 mmol, 67.8% yield).

Melting point: 145.5°–156.4° C.

$^1$H-NMR Spectrum (CDCl$_3$, TMS, ppm):

δ 1.80 (4H, m), 2.40 (4H, m), 6.00 (1H, br, s), 6.85 (1H, d, J$_{HF}$=6.5 Hz), 7.17 (1H, d, J$_{HF}$=9.0 Hz).

IR Spectrum (KBr cm$^{-1}$): 3440, 1785, 1720, 1530, 1430, 1395, 1185.

REFERENCE EXAMPLE 7

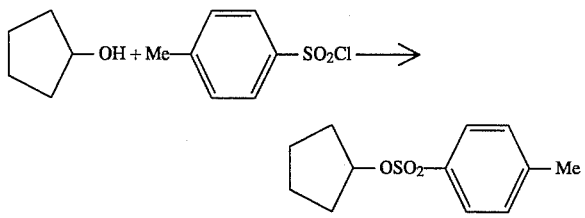

Cyclopentanol (50.0 g, 0.58 mol) and p-toluenesulfonyl chloride (120 g, 0.629 mol) were dissolved in pyridine (200 ml), and the solution was poured into ice-water (about 1 liter), followed by thoroughly stirring. The precipitated solid was filtered and dried to obtain cyclopentyl p-toluenesulfonate as a white solid (94.9 g, 0.390 mol, 68.1% yield).

Melting point: below 30° C.

$^1$H-NMR Spectrum (CDCl$_3$, TMS, ppm):

δ 1.23–2.07 (8H, m), 2.45 (3H, s), 4.98 (1H, m), 7.38 (2H, d, J=9.0 Hz), 7.85 (2H, d, J=9.0 Hz).

REFERENCE EXAMPLE 8

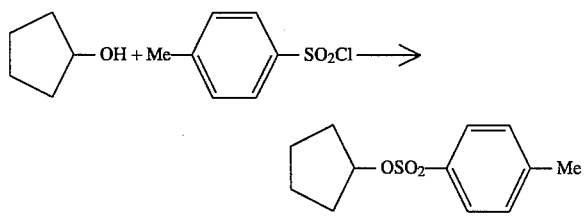

Cyclopentanol (10 g, 0.116 mol), p-toluenesulfonyl chloride (24.3 g, 0.128 mol) and ether (100 ml) were charged into a 200 cc round-bottom flask and dissolved. Then, potassium hydroxide (32.5 g, 0.58 mol) in a powder form was added slowly thereto while cooling below 10° C. in a water bath. After addition, the mixture was stirred as it was for additional 2 hours. After completion of the reaction, the mixture was poured into ice-water (20 ml), and the organic layer and the aqueous layer were separated. The organic layer was dried, and concentrated under reduced pressure to obtain cyclopentyl p-toluenesulfonate as a pale yellow viscous liquid (22.0 g, 81.8% yield).

REFERENCE EXAMPLE 9

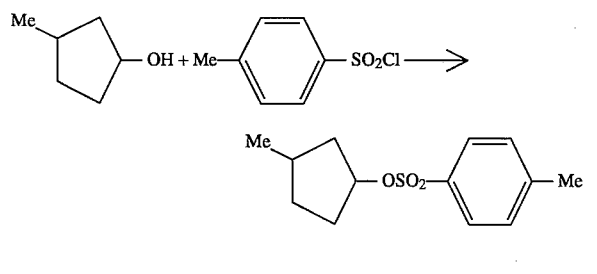

3-Methylcyclopentanol (5.0 g, 49.9 mmol) was reacted with p-toluenesulfonyl chloride in pyridine (50 ml) in the same procedure as in Reference Example 7 to obtain 3-methylcyclopentyl p-toluenesulfonate (11.7 g, 46.2 mmol, 92.5% yield).

$^1$H-NMR Spectrum (CDCl$_3$, TMS, ppm):

δ 0.93 and 1.00 (total 3H, each d, J=6.0 Hz), 1.20–2.30 (7H, m), 2.48 (3H, s), 4.97 (1H, m), 7.38 (1H, d, J=8.0 Hz), 7.85 (1H, d, J=8.0 Hz).

REFERENCE EXAMPLE 10

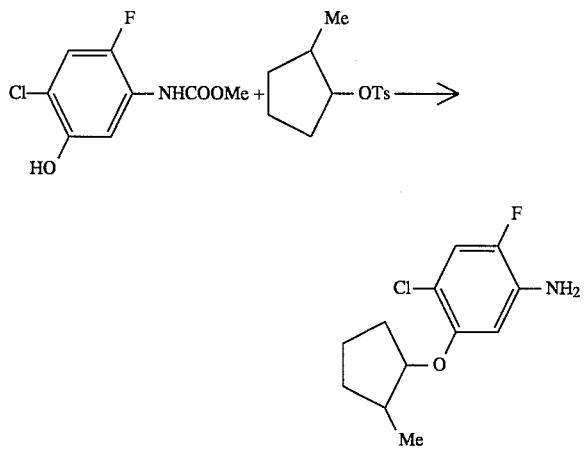

A solution of methyl N-(2-fluoro-4-chloro-5-hydroxyphenyl)carbamate (1.53 g, 6.98 mmol) synthesized by the process described in Reference Example 8, 2-methylcyclopentyl p-toluenesulfonate (1.78 g, 6.99 mmol) and N,N-dimethylformamide (15 ml) was charged into a 50 cc round-bottom flask, and then potassium hydroxide (400 mg, 7.15 mmol) in a powder form was added thereto, followed by stirring for 7 hours while heating on an oil bath at 80 to 100° C. After completion of the reaction, the reaction solution was cooled to room temperature, 2N hydrochloric acid (50 ml) was added thereto, and the mixture was extracted with ethyl acetate (20 ml×8). The organic layers were combined, washed with a saturated aqueous solution of sodium chloride and dried over anhydrous magnesium sulfate. The drying agent was removed by filtration, and the solvent was distilled off under reduced pressure to obtain a crude product (1.51 g). The product was purified by silica gel column chromatography (development solvent: hexane/ethyl acetate=17/3) to obtain 2-fluoro-4-chloro-5-(2-methylcyclopentyl)oxyaniline as a colorless oily substance (668 mg, 2.73 mmol, 40% yield).

Colorless transparent oily substance $^1$H-NMR Spectrum (CDCl$_3$, TMS, ppm):

δ 1.04 and 1.15 (total 3H, each d, J=7.0 Hz and 7.0 Hz), 1.40–2.40 (7H, m), 3.66 (2H, br s), 4.15 and 4.42 (total 1H, each m), 6.35 (1H, d, J$_{HF}$=9.2 Hz), 6.98 (1H, d, J$_{HF}$=11.9 Hz).

IR Spectrum (neat, cm$^{-1}$): 3425, 2980, 2900, 1630, 1510, 1245, 1190.

REFERENCE EXAMPLE 11

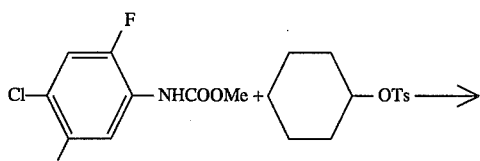

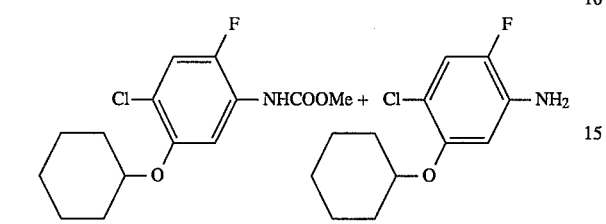

Methyl N-(2-fluoro-4-chloro-5-hydroxyphenyl)carbamate (1.00 g, 4.56 mmol) synthesized by the process described in Reference Example 3, cyclohexyl p-toluenesulfonate (1.20 g, 4.73 mmol), potassium carbonate (635 mg, 4.95 mmol), a catalytic amount of potassium iodide and N,N-dimethylformamide (20 ml) as a solvent were charged into a 100 cc round-bottom flask, and stirred on an oil bath at 80° C. After completion of the reaction, the reaction solution was cooled to room temperature, 1N hydrochloric acid (100 ml) was added thereto, and the mixture was extracted with ethyl acetate (20 ml×3). The organic layers were combined, washed with water and a saturated aqueous solution of sodium chloride and dried over anhydrous magnesium sulfate. The drying agent was removed by filtration, the solvent was distilled off under reduced pressure to obtain a crude product (875 mg). The product was isolated and purified by silica gel column chromatography (development solvent: hexane/ethyl acetate=9/1) to obtain methyl N-(2-fluoro-4-chloro-5-cyclohexyloxyphenyl)carbamate (12 mg, 0.46 m 8.1% yield), 2-fluoro-4-chloro-5-cyclohexyloxyaniline (213 mg, 0.87 mmol, 19% yield) and the unreacted starting material, methyl N-(2-fluoro-4-chloro-5-hydroxyphenyl)-carbamate (540 mg, 2.48 mmol, 54% recovery ratio). [Methyl N-(2-fluoro-4-chloro-5-cyclohexyloxyphenyl)carbamate]

White needle crystals

Melting point:

$^1$H-NMR Spectrum (CDCl$_3$, TMS, ppm):

δ 1.03–2.08 (10H, m), 3.80 (3H, s), 4.22 (1H, m), 7.10 ( 1H, d, J$_{HF}$=10.5 Hz), 7.88 ( 1H, d, J$_{HF}$=7.3 Hz).

[2-Fluoro-4-chloro-5-cyclohexyloxyaniline]

Colorless transparent oily substance $^1$H-NMR Spectrum (CDCl$_3$, TMS, ppm):

δ 1.15–2.06 (10H, m), 3.46 (2H, br, s), 4.10 (1H, m), 6.39 (1H, d, J$_{HF}$=9.0 Hz), 6.97 (1H, d, J$_{HF}$=11.5 Hz).

IR Spectrum (neat, cm$^{-1}$): 3500, 3400, 2940, 2860, 1630, 1505, 1240, 1190.

REFERENCE EXAMPLE 12

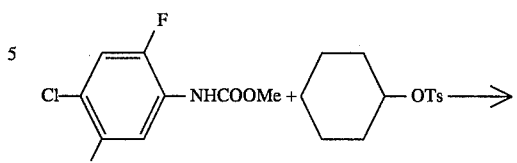

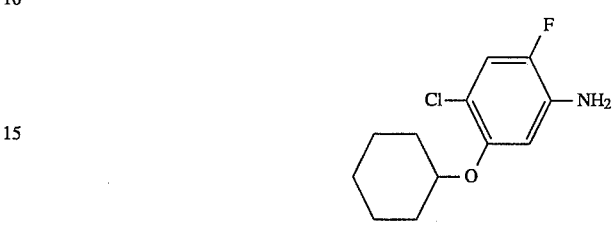

Methyl N-(2-fluoro-4-chloro-hydroxyphenyl)carbamate (2.03 g, 9.23 mmol), cyclohexyl p-toluenesulfonate (2.51 g, 9.85 mmol) and N,N-dimethylformamide (30 ml) were charged into a 100 cc round-bottom flask, and then potassium hydroxide (1.0 g, 17.8 mmol) in a powder form was added thereto. The mixture was stirred for 4 hours on an oil bath at 80° C. After completion of the reaction, the reaction solution was cooled to room temperature, 1N hydrochloric acid (100 ml) was added thereto, and the mixture was extracted with ethyl acetate (20 ml×8). The organic layers were combined, washed with water and a saturated aqueous solution of sodium chloride and dried over anhydrous magnesium sulfate. The drying agent was removed by filtration, and the solvent was distilled off under reduced pressure to obtain a crude product. The product was isolated and purified by silica gel column chromatography (development solvent: hexane/ethyl acetate=9/1) to obtain 2-fluoro-4-chloro-5-cyclohexyloxyaniline (574 mg, 2.36 mmol, 26% yield) and the unreacted starting material, methyl N-(2-fluoro-4-chloro-5-hydroxyphenyl)carbamate (1.22 g, 5.54 mmol, 60% recovery ratio). The spectral data and the like are as shown in Reference Example 11.

REFERENCE EXAMPLE 13

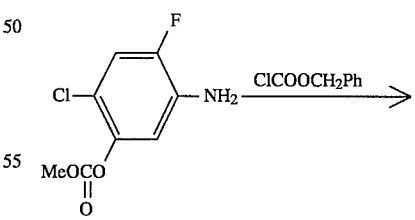

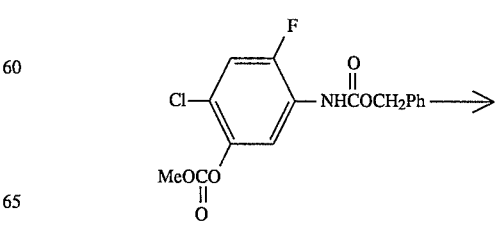

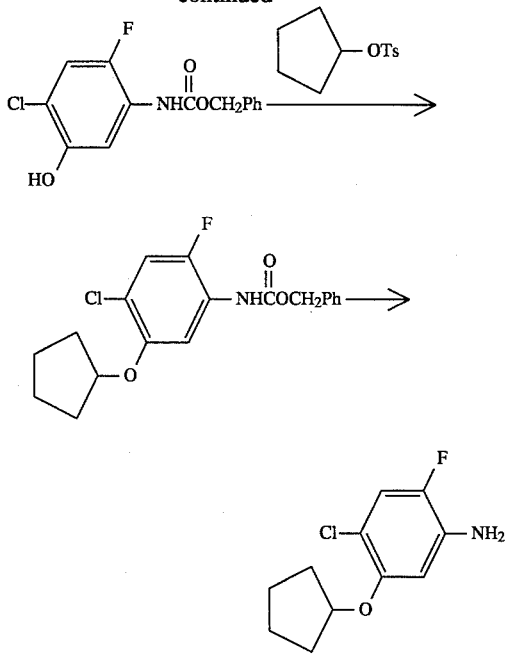

2-Fluoro-4-chloro-5-methoxycarbonuloxyaniline (2.00 g, 6.86 mmol), potassium carbonate (1.42 g, 10.3 mmol), benzyl chloroformate (1.17 g, 6.86 mmol) and acetone (20 ml) as a solvent were charged into a 100 cc two-necked flask, and heated for 2 hours while refluxing. After completion of the reaction, the mixture was added to 1H hydrochloric acid (50 ml), and extracted with ethyl acetate (50 ml×3). After drying, the organic layer was concentrated to obtain substantially pure benzyl N-(2-fluoro-4-chloro-5-methoxycarbonyloxyphenyl)carbamate as a solid (2.21 g, 91.1% yield).

Melting point: 70°–72° C.

$^1$H-NMR Spectrum (CDCl$_3$, TMS, ppm):

δ 3.62 (3H, s), 3.96 (2H, s), 6.59 (1H, d, J=7.5 Hz), 7.01 (1H, d, J=10.0 Hz), 7.20 (1H, br s), 7.10–7.50 (5H, m).

Benzyl N-(2-fluoro-4-chloro-5-methoxycarbonyloxyphenyl)carbamate (1.77 g, 5.0 mmol) obtained as described above and potassium carbonate (0.69 g, 5.0 mmol) were charged into a 50 cc flask, and methanol (30 ml) as a solvent was added thereto, followed by stirring at 50 to 60° C. for 2 hours. After completion of the reaction, the mixture was cooled to room temperature and poured into cooled 2N hydrochloric acid (60 ml). The mixture was stirred thoroughly, and the precipitated benzyl N-(2-fluoro-4-chloro-5-hydroxyphenyl)carbamate as a white solid (1.36 g, 4.60 mmol 92% yield) was isolated by filtration and well dried.

Melting point: 70°–72° C.

$^1$H-NMR Spectrum (CDCl$_3$+DMSO-d$_6$, TMS, ppm):

δ 5.25 (2H), 7.10 (1H, d, J=11.5 Hz), 7.49 (5H, s), 7.85 (1H, d, J=8.6 Hz), 9.47 (1H, br s).

Then, benzyl N-(2-fluoro-4-chloro-5-hydroxyphenyl)carbamate (12.2 g, 41.3 mmol), potassium carbonate (5.97 g, 432.1 mmol), cyclopentyl p-toluenesulfonate (11.2 g, 46.4 mmol) and acetone (150 ml) as a solvent were charged into a 500 cc round-bottom flask and heated for 9 hours while refluxing. After completion of the reaction, the reaction mixture was poured into 1N hydrochloric acid. After thoroughly stirring, the precipitated benzyl N-(2-fluoro-4-chloro-5-cyclopentyloxyphenyl)carbamate as a pale yellow solid (14.9 g, 40.9 mmol, 99% yield) was isolated by filtration and well dried.

$^1$H-NMR Spectrum (CDCl$_3$, TMS, ppm):

δ 1.48–2.07 (8H, m), 4.83 (1H, m), 5.26 (2H, s), 6.92 (1H, br s), 7.14 (1H, d, J$_{HF}$=11.5 Hz), 7.47 (5H, s), 7.93 (1H, d, J$_{HF}$=8.3 Hz).

Benzyl N-(2-fluoro-4-chloro-5-cyclopentyloxyphenyl)carbamate (2.00 g, 5.51 mmol) synthesized as described above, 5% Pd/C (100 mg) as a catalyst, and toluene (15 ml) as a solvent were charged into a 50 cc round-bottom flask, and the inside of the flask was replaced sufficiently with a hydrogen gas. Then, in a hydrogen gas atmosphere, the mixture was thoroughly stirred for 8 hours at 50° C. After completion of the reaction, the catalyst was separated by filtration, the resulting filtrate was dried with anhydrous magnesium sulfate. After separating the drying agent by filtration, the solvent was distilled off under reduced pressure from the filtrate to obtain quantitatively 2-fluoro-4-chloro-5cyclopentyloxyaniline (1.26 g) as a pale brown oily substance. The spectral data and the like are shown in Reference Example 1.

REFERENCE EXAMPLE 14

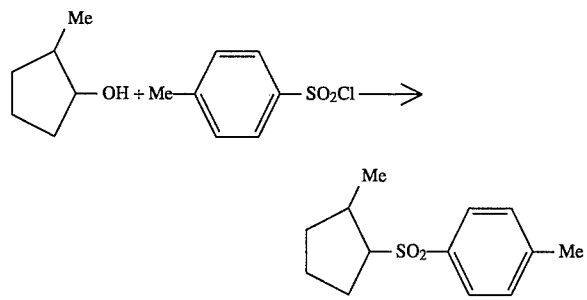

2-Methylcyclopentanol (21.06 g, 0.210 mol) and p-toluenesulfonyl chloride (48.3 g, 0.252 mol) were charged into a 500 cc three-necked flask equipped with a stirrer, and then pyridine (170 ml) was added dropwise thereto under ice-cooling. The mixture was stirred for 10 hours while gradually elevating the temperature to room temperature. After completion of the reaction, cold water (500 ml) was added to the reaction mixture, and the mixture was extracted with ether (200 ml×3). The organic layers were combined, washed successively with 2N hydrochloric acid, water and a saturated aqueous solution of sodium chloride, and dried with anhydrous magnesium sulfate. The drying agent was separated by filtration, and the solvent was distilled off under reduced pressure to obtain substantially pure 2-methylcyclopentyl p-toluenesulfonate as a colorless transparent oily substance (49.7 g, 0.195 mol, 93% yield).

Colorless transparent oily substance $^1$H-NMR Spectrum (CDCl$_3$, TMS, ppm):

δ 0.85 (3H, d, J=7.5 Hz), 1.41–2.10 (7H, m), 2.43 (3H, s), 4.42 and 4.80 (total 1H, each m), 7.33 (2H, d, J$_{HF}$=9.0 Hz), 7.80 (2H, d, J$_{HF}$=9.0 Hz).

REFERENCE EXAMPLE 15

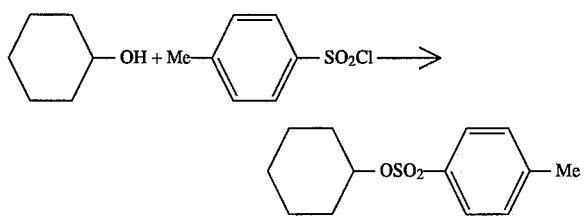

Cyclohexanol (5.01 g, 50.0 mmol) and p-toluenesulfonyl chloride (10.6 g, 55.6 mmol) were charged into a 100 cc round-bottom flask, and then pyridine (20 ml) was added dropwise thereto under ice-cooling. The mixture was stirred for 8 hours while gradually elevating the temperature to room temperature. After completion of the reaction, cold water (500 ml) was added to the reaction mixture, and the mixture was extracted with ether (100 ml×3). The organic layers were combined, washed successively with 2N hydrochloric acid, water and a saturated aqueous solution of sodium chloride, and dried with anhydrous magnesium sulfate. The drying agent was separated by filtration, and the solvent was distilled off under reduced pressure to obtain substantially pure cyclohexyl p-toluenesulfonate as a white solid (12.7 g, 49.9 mmol, 99% yield).

$^1$H-NMR Spectrum (CDCl$_3$, TMS, ppm):

δ 1.00–1.93 (10H, m), 2.43 (3H, s), 4.30–4.64 (1H, m), 7.30 (2H, d, $J_{HF}$=9.0 Hz), 7.78 (2H, d, $J_{HF}$=9.0 Hz).

REFERENCE EXAMPLE 16

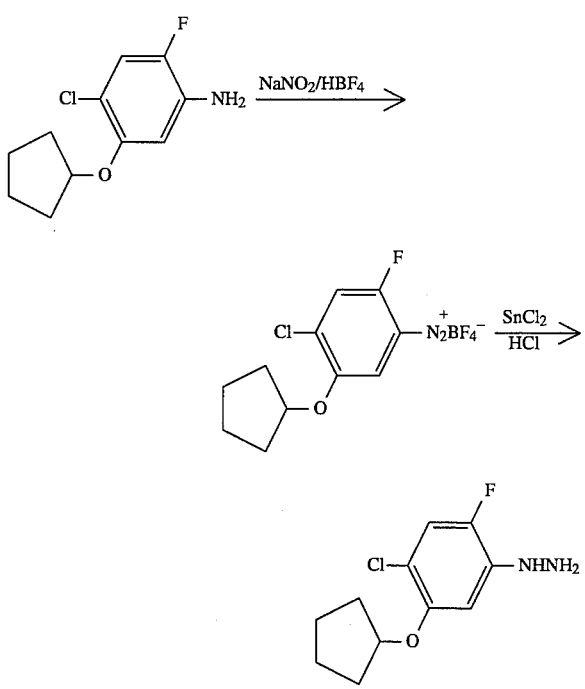

2-Fluoro-4-chloro-5-cyclopentyloxyaniline (23.0 g, 0.10 mol) synthesized by the process described in Reference Example 1, 3, 4 or 13 was dissolved in acetonitrile (50 ml), and 42% borofluoric acid (150 ml) was added thereto. After stirring for 30 minutes at room temperature, an aqueous solution (150 ml) of sodium sulfite (20 g, 0.280 mol) was added slowly thereto at 0° C. to 5° C. After stirring for 2 hours at that temperature, the solid formed was separated by filtration and washed with ice-water and then ethyl acetate/hexane (1/6). By drying it thoroughly, 2-fluoro-4-chloro-5-cyclopentyloxyphenyldiazonium fluoro-borate was obtained as a grey-white solid (29.5 g, 89.4% yield).

Melting point: 147°–150° C. (decomposition)

$^1$H-NMR Spectrum (CDCl$_3$, TMS, ppm):

δ 1.38–2.17 (8H, m), 4.88 (1H, m), 7.57 (1H, d, $J_{HF}$=9.0 Hz), 8.10 (1H, d, $J_{HF}$=5.0 Hz).

IR Spectrum (neat, cm$^{-1}$): 3130, 2975, 2280, 1490, 525.

To a solution of tin (II) chloride monohydrate (200 g, 0.886 mol) dissolved in concentrated hydrochloric acid (200 ml) and THF (200 ml) was added a THF (200 ml) solution of 2-fluoro-4-chloro-5-cyclopentyloxyphenyl-diazonium fluoroborate (31.3 g, 0.094 mol) under cooling at 0 to 5° C. After stirring for 8 hours at that temperature, an aqueous solution (1,000 ml) of potassium hydroxide (160 g) was added thereto. The solid that was formed was separated by filtration, and the filtrate was extracted with ethyl acetate (1,000 ml×3). The extract was washed with a saturated aqueous solution of sodium chloride (1,000 ml), and dried over anhydrous magnesium sulfate. The drying agent was separated by filtration, and the solvent was distilled off under reduced pressure to obtain 2-fluoro-4-chloro-5cyclopentyloxyphenylhydrazine as brown crystals (20.9 g, 85.6% yield).

Melting point: 77°–79° C.

$^1$H-NMR Spectrum (CDCl$_3$, TMS, ppm):

δ 1.35–2.1 (8H, m), 3.85 (1H, br, s), 4.75 (1H, m), 6.60 (1H, d, $J_{HF}$=8.0 Hz), 6.95 (1H, d, $J_{HF}$=14.0 Hz).

IR Spectrum (KBr disk, cm$^{-1}$): 3350, 2980, 1610, 1510, 1175, 855.

MS Spectrum (m/e) 246 (M$^+$, 5%), 244 (M$^+$, 17%), 176 (100%), 41 (61%). Elementary Analysis (Calculated Values, $C_{11}H_{14}N_2OClF$, %):

C, 53.80 (53.99);

H, 5.74 (5.77);

N, 11.35 (11.45).

Next, the present invention is further illustrated by the preparation examples of the herbicidal agent comprising the compound of the present invention as an active ingredient, and the examples describing herbicidal effect by the herbicidal agent. The parts are shown by weight.

PREPARATION EXAMPLE 1 (Emulsifiable Agent)

20 parts of Compound 10 of the present invention, 35 parts of xylene, 40 parts of cyclohexanone and 5 parts of Sorbol 900A (Toho Chemical Co., Ltd.) were uniformly mixed to obtain an emulsifiable agent. Other compounds of the present invention were also processed as described above to obtain emulsifiable agents.

PREPARATION EXAMPLE 2 (Wettable Powder)

A mixture of 50 parts of Compound 10 of the present invention, 25 parts of diatomaceous earth, 22 parts of clay and 3 parts of Lunox R100C (Toho Chemical Co., Ltd.) was uniformly mixed and ground to obtain a wettable powder. Other compounds of the present invention were also processed as described above to obtain wettable powders.

PREPARATION EXAMPLE 3 (Granule Agent)

A mixture of 5 parts of Compound 10 of the present invention, 85 parts of bentonite, 55 parts of talc and 5 parts of sodium lignin sulfonate was uniformly mixed and ground, and then kneaded by adding water. The mixture was granulated by extruding from a granulator, dried, and regulating the grains to obtain a granule agent.

TEST EXAMPLE 1 (Effect on Weeds in Paddy Field)

Wagner pots of 1/5000 Are were filled with the soil of paddy field, and seeded with the seeds of early water-grass, Monochoria, and Japanese bulrush, and transplanted with a rice plant (Species: Nihonbare) at a 2–3 leaf stage. The pots were maintained while perfusing with water. After 5 days, the water surface was treated with a diluted solution of the compound of the present invention formulated in a wettable powder or an emulsifiable agent according to the preparation examples in the predetermined amounts of 5, 2.5, 1 and 0.5 g per Are. On the 20th day after the treatment, the herbicidal effect on the test weeds and the damage to the rice plant were investigated according to the following standards of judgement, whereby the results shown in Table 2 were obtained.

| Standards of Judgement | | | |
|---|---|---|---|
| Degree of Killing of Weeds | Proportion of Remaining Weeds (%) | Damage | Growing Proportion |
| 0 | 81–100 | − | None |
| 1 | 61–80 | + | Very slight damage |
| 2 | 41–60 | ++ | Slight damage |
| 3 | 21–40 | +++ | Middle damage |
| 4 | 6–20 | ++++ | Severe damage |
| 5 | 0–5 | X | Withering |

A commercially available compound (A) was used as a control compound, and, using the same preparation and treatment methods, the weed-killing activity and the damage to the crops were investigated according to the same standards of judgement. The results thereof are also shown.

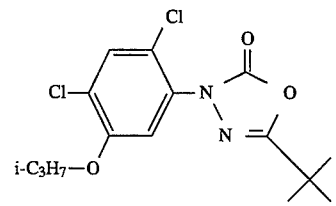

Control Compound A (Ronstar)

TABLE 2

Effects by Soil Pre-treatment of Soil in Paddy Field

| Test Compound | Amount of Application (g/a) | Herbicidal Activity | | | | | Damage to Rice Plant |
|---|---|---|---|---|---|---|---|
| | | E. Watergrass | M. Vaginalis | Other Annual Broad Leaf Weeds | N. Spikerush | Japanese Bulrush | |
| 10 | 5 | 5 | 5 | 5 | 5 | 5 | + |
| | 2.5 | 5 | 5 | 5 | 5 | 5 | − to + |
| | 1 | 5 | 5 | 5 | 5 | 5 | − |
| | 0.5 | 5 | 5 | 5 | 5 | 4 | − |
| 11 | 5 | 5 | 5 | 5 | 5 | 5 | + |
| | 2.5 | 5 | 5 | 5 | 5 | 5 | − to + |
| | 1 | 5 | 5 | 5 | 5 | 5 | − |
| | 0.5 | 5 | 5 | 5 | 4 | 5 | − |
| 12 | 5 | 5 | 5 | 5 | 5 | 5 | − to + |
| | 2.5 | 5 | 4 | 5 | 4 | 4 | − |
| | 1 | 5 | 4 | 5 | 4 | 4 | − |
| | 0.5 | 4–5 | 4 | 5 | 4 | 4 | − |
| 13 | 5 | 5 | 5 | 5 | 5 | 5 | + |
| | 2.5 | 5 | 5 | 5 | 5 | 5 | − to + |
| | 1 | 5 | 5 | 5 | 5 | 5 | − |
| | 0.5 | 5 | 5 | 5 | 4 | 5 | − |
| 26 | 5 | 5 | 5 | 5 | 5 | 5 | + |
| | 2.5 | 5 | 5 | 5 | 5 | 5 | − to + |
| | 1 | 5 | 5 | 5 | 5 | 4 | − |
| | 0.5 | 5 | 4 | 5 | 4 | 4 | − |
| 28 | 5 | 5 | 5 | 5 | 5 | 4 | + |
| | 2.5 | 5 | 5 | 5 | 5 | 4 | − to + |
| | 1 | 5 | 5 | 5 | 5 | 3 | − |
| | 0.5 | 4–5 | 4 | 5 | 4 | 3 | − |
| A | 5 | 5 | 5 | 5 | 5 | 5 | ++ |
| | 2.5 | 5 | 5 | 5 | 4 | 5 | + |
| | 1 | 4 | 5 | 5 | 3 | 5 | + |
| | 0.5 | 3 | 5 | 5 | 2 | 4 | − |

TEST EXAMPLE 2 (Effects by Field Soil Treatment)

Vats having a surface area of 16×10 cm² and a depth of 7 cm were filled with the field soil, and seeded with seeds of southern crabgrass, common lambsquarters, barnyard grass, and soybean and corn. The vats were then covered with the soil in 1 cm thick. Next day, a diluted solution of the compound of the present invention Formulated in a wettable powder or an emulsifiable agent prepared according to the preparation examples dropped uniformly onto the covered soil in the predetermined amounts of 20, 10 and 5 g per Are. On the 20th day after the application, the herbicidal activity on the test weeds, and the damage to the soybean and the corn were investigated in the same manner as in Test Example 1. The results thereof are shown in Table 3.

TABLE 3

Effects by Field Soil Treatment

| Test Compound | Amount of Application (g/a) | Southern Crabgrass | Common Lambsquarters | Barnyard Grass | Damage Soybean | Corn |
|---|---|---|---|---|---|---|
| 10 | 20 | 5 | 5 | 5 | + | − to + |
|    | 10 | 5 | 5 | 5 | + | − |
|    | 5  | 5 | 5 | 5 | − to + | − |
| 11 | 20 | 5 | 5 | 4 | + | − to + |
|    | 10 | 3–4 | 5 | 3 | − to + | − |
|    | 5  | 3 | 4 | 2–3 | − | − |
| 12 | 20 | 5 | 5 | 5 | ++ | + |
|    | 10 | 5 | 5 | 5 | + | − to + |
|    | 5  | 4 | 5 | 5 | + | − |
| 13 | 20 | 5 | 5 | 4 | + | − to + |
|    | 10 | 3–4 | 5 | 3–4 | − to + | − |
|    | 5  | 3 | 4 | 3 | − | − |
| 26 | 20 | 5 | 5 | 5 | ++ | +++ |
|    | 10 | 5 | 5 | 5 | + | ++ |
|    | 5  | 5 | 5 | 5 | + | + |
| 28 | 20 | 5 | 5 | 5 | + | + |
|    | 10 | 5 | 5 | 5 | − to + | − to + |
|    | 5  | 5 | 5 | 5 | − | − to + |
| A  | 20 | 5 | 5 | 5 | ++ | ++ |
|    | 10 | 4 | 5 | 5 | ++ | + |
|    | 5  | 3 | 4 | 4 | + | + |

TEST EXAMPLE 3 (Effects by Foliar Application)

Vats having a surface area of 16×11 cm² and a depth of 7 cm were filled with the field soil, and seeded with seeds of southern crabgrass, common lambsquarters, barnyard grass, and soybean. After 15 days, a diluted solution of the compound of the present invention formulated in a wettable powder or an emulsifiable agent was applied by a spray treatment at the predetermined concentrations in a water amount of 10 liters per Are. On the 20th day after the treatment, the weed-killing effect on the test weeds and the damage to the soybean were investigated in the same manner as in Test Example 1. The results thereof are shown in Table 4.

TABLE 4

Effects by Foliar Application

| Test Compound | Amount of Application ppm | Southern Crabgrass | Common Lamgsquarters | Barnyard grass |
|---|---|---|---|---|
| 10 | 1000 | 5 | 5 | 5 |
|    | 200  | 5 | 5 | 5 |
|    | 50   | 4 | 5 | 5 |
| 11 | 1000 | 5 | 5 | 5 |
|    | 200  | 5 | 5 | 5 |
|    | 50   | 4 | 5 | 4 |
| 12 | 1000 | 5 | 5 | 5 |
|    | 200  | 5 | 5 | 5 |
|    | 50   | 4 | 5 | 5 |
| 13 | 1000 | 5 | 5 | 5 |
|    | 200  | 5 | 5 | 5 |
|    | 50   | 4 | 5 | 4 |
| 26 | 1000 | 5 | 5 | 5 |
|    | 200  | 5 | 5 | 5 |
|    | 50   | 4 | 5 | 5 |
| 28 | 1000 | 5 | 5 | 5 |
|    | 200  | 5 | 5 | 5 |
|    | 50   | 4 | 5 | 5 |
| A  | 1000 | 5 | 5 | 5 |
|    | 200  | 4–5 | 5 | 5 |
|    | 50   | 2 | 4–5 | 4 |

We claim:

1. A benzene derivative substituted with a heterocyclic ring represented by the formula:

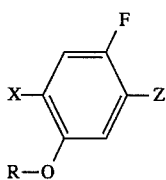

wherein R represents a cycloalkyl group having 3 to 8 carbon atoms, X represents a halogen atom, and Z represents

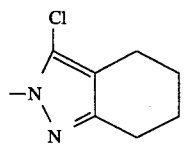

in which said cycloalkyl group may be substituted with an alkyl group having 1 to 6 carbon atoms.

2. A compound as claimed in claim 1, wherein R is a cyclopentyl group which may be substituted with an alkyl group having 1 to 6 carbon atoms.

3. A herbicidal composition comprising, as an active ingredient, a benzene derivative substituted with a heterocyclic ring represented by the formula:

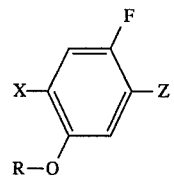

wherein R represents a cycloalkyl group having 3 to 8 carbon atoms, X represents a halogen atom, and Z represents

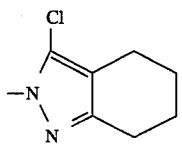

in which said cycloalkyl group may be substituted with an alkyl group having 1 to 6 carbon atoms.

4. A herbicidal composition as claimed in claim 3, wherein R is a cyclopentyl group which may be substituted with an alkyl group having 1 to 6 carbon atoms.

* * * * *